United States Patent
Gallucci et al.

(10) Patent No.: US 12,221,463 B2
(45) Date of Patent: Feb. 11, 2025

(54) METHOD OF PROMOTING WOUND HEALING BY INHIBITING CCR3

(71) Applicant: The Board of Regents of the University of Oklahoma, Norman, OK (US)

(72) Inventors: Randle M. Gallucci, Edmond, OK (US); Kaitlin N. Calhoun, Greeley, CO (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 450 days.

(21) Appl. No.: 17/396,235

(22) Filed: Aug. 6, 2021

(65) Prior Publication Data

US 2022/0041668 A1  Feb. 10, 2022

Related U.S. Application Data

(60) Provisional application No. 63/062,535, filed on Aug. 7, 2020.

(51) Int. Cl.
| | | |
|---|---|---|
| A61K 39/395 | (2006.01) | |
| A61P 17/02 | (2006.01) | |
| C07K 14/47 | (2006.01) | |
| C07K 16/00 | (2006.01) | |
| C07K 16/24 | (2006.01) | |
| A61K 38/00 | (2006.01) | |
| A61K 39/00 | (2006.01) | |

(52) U.S. Cl.
CPC ........ *C07K 14/4703* (2013.01); *A61K 39/395* (2013.01); *A61P 17/02* (2018.01); *C07K 16/00* (2013.01); *C07K 16/24* (2013.01); *A61K 38/00* (2013.01); *A61K 2039/505* (2013.01)

(58) Field of Classification Search
None
See application file for complete search history.

(56) References Cited

U.S. PATENT DOCUMENTS

| | | |
|---|---|---|
| 4,172,124 A | 10/1979 | Koprowski et al. |
| 4,816,397 A | 3/1989 | Boss et al. |
| 4,816,567 A | 3/1989 | Cabilly et al. |
| 4,946,778 A | 8/1990 | Ladner et al. |
| 5,225,539 A | 7/1993 | Winter |
| 5,270,163 A | 12/1993 | Gold et al. |
| 5,840,867 A | 11/1998 | Toole et al. |
| 6,180,348 B1 | 1/2001 | Li |
| 6,207,155 B1 | 3/2001 | Grimaldi et al. |
| 6,331,541 B1 | 12/2001 | Ko et al. |
| 6,566,376 B1 | 5/2003 | Baxter et al. |
| 6,627,629 B2 | 9/2003 | Ko et al. |
| 6,635,251 B1 | 10/2003 | Williams et al. |
| 6,521,592 B2 | 12/2003 | Ko et al. |
| 6,699,843 B2 | 3/2004 | Pietras et al. |
| 6,706,735 B2 | 3/2004 | Watson et al. |
| 6,759,411 B2 | 3/2004 | Watson et al. |
| 6,780,857 B2 | 8/2004 | Ko et al. |
| 6,821,964 B2 | 11/2004 | Colon-Cruz et al. |
| 6,822,087 B1 | 11/2004 | Renzi |
| 6,864,380 B2 | 3/2005 | Wacker et al. |
| 6,875,776 B2 | 4/2005 | Ko et al. |
| 6,897,234 B2 | 5/2005 | Ko et al. |
| 6,903,115 B2 | 6/2005 | Rigby et al. |
| 6,906,066 B2 | 6/2005 | Ko et al. |
| 6,919,368 B2 | 7/2005 | Ko et al. |
| 6,946,546 B2 | 9/2005 | Vaughan et al. |
| 6,949,546 B2 | 9/2005 | Ko et al. |
| 6,960,666 B2 | 11/2005 | Duncia et al. |
| 6,974,869 B2 | 12/2005 | DeLucca |
| 6,984,643 B2 | 1/2006 | Du Bois et al. |
| 6,984,651 B2 | 1/2006 | Duncia et al. |
| 10,106,588 B2 | 10/2018 | Herman |
| 2002/0147312 A1 | 10/2002 | O'Keefe et al. |
| 2004/0014132 A1 | 1/2004 | Vaughan et al. |
| 2004/0063779 A1 | 4/2004 | Dollinger et al. |

(Continued)

FOREIGN PATENT DOCUMENTS

| | | |
|---|---|---|
| EP | 0125023 B1 | 6/1991 |
| EP | 0120694 B1 | 7/1993 |

(Continued)

OTHER PUBLICATIONS

Sen, et al.; "Human Skin Wounds: A Major and Snowballing Threat to Public Health and the Economy," Wound Repair Regen. (2009) 17(6):763-771.

(Continued)

*Primary Examiner* — Christine J Saoud
*Assistant Examiner* — Jon M Lockard
(74) *Attorney, Agent, or Firm* — Dunlap Codding, P.C.

(57) ABSTRACT

A method of treating a skin wound in a subject by administering at least one inhibitor of C-C chemokine receptor type-3 (CCR3) and/or at least one inhibitor of a CCR3 ligand, thereby causing increased activity of keratinocytes adjacent the skin wound, wherein epithelialization of the skin wound is promoted, and wherein the increased activity of keratinocytes is at least one of (1) increased proliferation of the keratinocytes and (2) increased migration of the keratinocytes adjacent the skin wound. The skin wound may be a chronic wound or an acute wound for example. The inhibitor may be, for example, an antibody or antibody fragment, a small molecule, or an siRNA able to inhibit expression of CCR3.

10 Claims, 29 Drawing Sheets
(4 of 29 Drawing Sheet(s) Filed in Color)
Specification includes a Sequence Listing.

(56) References Cited

U.S. PATENT DOCUMENTS

| | | |
|---|---|---|
| 2004/0191255 A1 | 9/2004 | Lillard, Jr. et al. |
| 2005/0069955 A1 | 3/2005 | Plaksin et al. |
| 2005/0070582 A1 | 3/2005 | Li et al. |
| 2005/0153979 A1 | 7/2005 | Anderskewitz et al. |
| 2005/0176708 A1 | 8/2005 | Luckhurst et al. |
| 2005/0182094 A1 | 8/2005 | Sanganee et al. |
| 2005/0182095 A1 | 8/2005 | Ting et al. |
| 2005/0191702 A1 | 9/2005 | Mack et al. |
| 2005/0197325 A1 | 9/2005 | Batt et al. |
| 2005/0197373 A1 | 9/2005 | Batt et al. |
| 2005/0222118 A1 | 10/2005 | Le Grand et al. |
| 2005/0234034 A1 | 10/2005 | Pennell et al. |
| 2007/0190055 A1 | 8/2007 | Ambati |

FOREIGN PATENT DOCUMENTS

| | | |
|---|---|---|
| EP | 0239400 B1 | 8/1994 |
| EP | 0194276 B2 | 1/2002 |
| WO | 8601533 A1 | 3/1986 |

OTHER PUBLICATIONS

Yates, et al.; "Delayed Reepithelialization and Basement Membrane Regeneration After Wounding in Mice Lacking CXCR3," Wound Repair Regen. (2009) 17(1):34-41.

Yates, et al.; "Skin Wound Healing and Scarring: Fetal Wounds and Regenerative Restitution," Birth Defects Res C Embryo Today (2012) 96(4):325-333.

Yawalkar, et al; "Enhanced Expression of Eotaxin and COR3 in Atopic Dermatitis," The Society for Investigative Dermatology (1999) 113(1):43-48.

Ying, et al.; "Eosinophil Chemotactic Chemokines (Eotaxin, Eotaxin-2, RANTES, Monocyte Chemnoattractant Protein-3 (MCP-3), and MCP-4), and C—C Chemokine Receptor 3 Expression in Bronchial Biopsies from Atopic and Nonatopic (Intrinsic) Asthmatics," The Journal of Immunology (1999) 163:6321-6329.

Zaja-Milatovic et al.; "CXC Chemokines and Their Receptors: a Case for a Significant Biological Role in Cutaneous Wound Healing," Histol Histopathol. (2008) 23(11):1399-1407.

Abreu-Velez, et al. " Collagen IV Normal Skin and Pathological Processes", North American Journal of Medical Sciences (2012), 4(1); 1-8.

Baggiolini, Marco, "Cemokines and Leukocyte Traffic", Nature (1998), vol. 392, pp. 565-568.

Beasley, et al.; "Prevalence and Etiology of Asthma", J. Allergy Clin. Immunol. (2000), vol. 105, No. 2, Part 2, pp. S467-S472.

Beck, et al.; "Functional Analysis of the Chemokine Receptor CCR3 on Airway Epithelial Cells", The Journal of Immunology (2006), vol. 177, pp. 3344-3354.

Behm, et al.; "Cytokines, Chemokines and Growth Factors in Wound Healing", Journal of the European Academy of Dermatology and Venereology (202), vol. 26, pp. 812-820.

Bettinger, et al.; "Hyaluronic Acid Impedes Reepithelialization of Skin Graft Donor Sites," Journal of Burn Care & Rehabilitation (1996), vol. 17, No. 4, pp. 302-304.

Bird, et al.; "Single-Chain Antigen-Binding Proteins," Science (1988), vol. 242, No. 4877, pp. 423-426.

Browning, et al.; "Effect of Diabetes Mellitus and Hyperglycemia on the Proliferation of Human Tenon's Capsule Fibroblasts: Implications for Wound Healing after Glaucoma Drainage Surgery," Wound Repair and Regeneration (2005), vol. 13, No. 3, pp. 295-302.

Brett, et al.; "A Review of Collagen and Collagen-based Wound Dressings," Wounds (2008), 20(12):347-356.

Buskermolen, et al.; "Stimulation of Oral Fibroblast Chemokine Receptors Identifies CCR3 and CCR4 as Potential Wound Healing Targets," Journal of Cellular Physiology (2017), 232(11):2996-3005.

Fryer, et al.; "Neuronal Eotaxin and the Effects of CCR3 Antagonist on Airway Hyperreactivity and M2 Receptor Dysfunction," Journal of Clinical Investigation (2006), 116(1):228-236.

Galliano, et al.; "Quantitative and Reproducible Murine Model of Excisional Wound Healing," Wound Repair and Regeneration (2004), 12(4):485-492.

Gallucci, et al.; "Interleukin 6 Indirectly Induces Keratinocyte Migration," J Invest Dermatol (2004), 122:764-772.

Gaspar, et al.; "The Chemokine Receptor CCR3 Participates in Tissue Remodeling During Atopic Skin Inflammation," Journal of Dermatological Science (2013), 71(1):12-21.

Gillitzer, et al.; "Chemokines in Cutaneous Wound Healing," J of Leukoc Biol (2001), 69(4):314-321.

Gurtner, et al.; "Wound Repair and Regeneration," Nature (2008), 453(7193):314-321.

Kohler, et al.; "Continuous Cultures of Fused Cells Secreting Antibody of Predefined Specificity," Nature (1975), 256, pp. 495-497.

Köhler, et al.; "Derivation of Specific Antibody-producing Tissue Culture and Tumor Lines by Cell Fusion," Eur. J. Immunol. (1976), 6:511-519.

Komesu, et al.; "Effects of Acute Diabetes on Rat Cutaneous Wound Healing," Pathophysiology (2004), 11(2):63-67.

Kroeze, et al.; "Autocrine Regulatoin of Re-Epithelialization After Wounding by Chemokine Receptors CCR1, CCR10, CXCR1, CXCR2, and CXCR3," Journal of Investigative Dermatology (2012), 132(1):216-225.

Lee, et al.; "Interleukin 6 Function in the Skin and Isolated Keratinocytes is Modulated by Hyperglycemia," Journal of Immunology Research (2019), vol. 2019, Article ID 5087847, 9 pages.

Luster, Andrew D.; "Chemokines—Chemotactic Cytokines That Mediate Inflammation," New England Journal of Medicine (1998), 338(7):436-445.

Ma, W, et al.; "CCR3 is Essential for Skin Eosinophilla and Airway Hyperresponsiveness in a Murine Model of Allergic Skin Inflammation," Journal Clin. Invest. (2002), 109:621-628.

Milstein, et al.; "Antibodies to Major Histcompatability Antigens Produced by Hybrid Cell Lines," Nature (1977) 266:550-552.

Mor, et al.; "Blockade of CCL24 with a Monoclonal Antibody Ameliorates Experimental Dermal and Pulmonary Fibrosis," Ann Rheum Dis (2019) 78:1260-1268.

Morokata, et al.; "A Novel, Selective, and Orally Available Antagonist for CC Chemokine Receptor 3," J. Pharmacol. Exp. Ther. (2005), 317(1):244-250.

Nakamura, et al.; "A Specific CCR3 Chemokine Receptor Antagonist Inhibits Both Early and Late Phase Allergic Inflammation in the Conjunctiva," Immunologic Research (2005), 33(3):213-221.

National Institute for Health, Guide for the Care and Use of Laboratory Animals (NIH Publication 86-23) (2011).

Newman, et al.; "Primatization of Recombinant Antibodies for Immunotherapy of Human Diseases: A Macaque/Human Chimeric Antibody Against Human CD4," Bio/Technology (1992), 10:1455-1460.

Pampfer, et al.; "Interleukin 1β Mediates the Effect of High D-Glucose on the Secretion of TNF-α by Mouse Uterine Epithelial Cells," Cytokine (1999), 11(7):500-509.

Pastar, et al.; "Epithelialization in Wound Healing: A Comprehensive Review," Advances in Wound Care (2014) 3(7):445-464.

Petering, et al.; "Characterization of the CC Chemokine Receptor 3 on Human Keratinocytes," J. Invest Dermatol (2001), 116(4):549-555.

Proksch, et al.; "The Skin: An Indispensable Barrier," Experimental Dermatology (2008) 17:1063-1072.

Satish, Latha; "Chemokines as Therapeutic Targets to Improve Healing Efficiency of Chronic Wounds," Advances in Wound Care (2015), 4(11):651-659.

Sen, et al.; "Cutaneous Imaging Technologies in Acute Burn and Chronic Wound Care," Plast Reconstr Surg. (2017).

Spravchikov, et al.; "Glucose Effects on Skin Keratinocytes Implications for Diabetes Skin Complications," Diabetes (2001), 50:1627-1635.

(56) References Cited

OTHER PUBLICATIONS

Stojadinovic, et al.; "Deregulation of Keratinocyte Differentiation and Activation: A Hallmark of Venous Ulcers," J. Cell. Mol. Med. (2008), 12(6B):2675-2690.

Suzuki, et al.; "In Vitro and In Vivo Characterization of a Novel CCR3 Antagonist, YM-344031," Biochemical and Biophysical Research Communication (2006), 339:1217-1223.

Ting, et al.; "The Synthesis of Substituted Bipiperidine Amide Compounds as CCR3 Ligands: Antagonists Versus Agonists," Bioorganic & Medicinal Chemistry Letters (2005), 15:3020-3023.

Turabelidze, et al.; "Intrinsic Differences Between Oral and Skin Keratinocytes," PLOS ONE (2014) 9(9):e101480.

Usui et al.; "Keratinocyte Migration, Proliferation, and Differentiation in Chronic Ulcers from Patients With Diabetes and Normal Wounds," Journal of Histochemistry & Cytochemistry (2008) 56(7):687-696.

Wakugawa, et al.; "Expression of CC Chemokine Receptor 3 on Human Keratinocytes In Vivo and In Vitro—Upregulation by RANTES," Journal of Dermatological Science (2001) 25:229-235.

Wawersik, et al.; "Increased Levels of Keratin 16 Alter Epithelialization Potential of Mouse Skin Keratinocytes In Vivo and Ex Vivo," Molecular Biology of the Cell (2001) 12:3439-3450.

Wikramanayake, et al.; "Epidermal Differentiation in Barrier Maintenance and Wound Healing," Advances in Wound Care (2014) 3(3):272-280.

Willems, et al.; "Small Molecule Antagonists for Chemokine CCR3 Receptors," Medicinal Research Reviews (2010) 30(5):778-817.

Control

Wound

9
3a
$K_i$ CCR3 = 50 nM
$K_i$ H$_1$ = 8 nM

10
3b
$K_i$ CCR3 = 10 nM
$K_i$ H$_1$ = 25 nM

11
AZ10565259
(AZD3778)
$K_i$ CCR3 = 6 nM
$K_i$ H$_1$ = 32 nM
IC$_{50}$ hERG = < 16 μM

12
3AZ12436092
$K_i$ CCR3 = 0.63 nM
$K_i$ H$_1$ = 158 nM
$K_i$ hERG = 31 μM

13
Compound 1
$K_i$ CCR1 = 40 nM
$K_i$ CCR3 = 100 nM
$K_i$ H$_1$ = 5 μM

14
Compound 20
$K_i$ CCR3 = 2 nM
$K_i$ H$_1$ = 4 nM
$K_i$ hERG = 8.3 μM

15
Compound 60
$K_i$ CCR3 = 4 nM
$K_i$ H$_1$ = 5 nM
$K_i$ hERG = 12.5 μM

SB-297006

SB-329437

BMS-1

BMS-2

21a

21b

22

35 (GW-766994)

4 (DPC-168)

5 (BMS-639623)

METHOD OF PROMOTING WOUND HEALING BY INHIBITING CCR3

CROSS REFERENCE TO RELATED APPLICATIONS AND INCORPORATION BY REFERENCE STATEMENT

The present patent application claims priority under 37 CFR § 119(e) to United States Provisional Patent Application U.S. Ser. No. 63/062,535, filed on Aug. 7, 2020. The entire contents of the above-referenced application(s) are hereby expressly incorporated herein by reference.

STATEMENT REGARDING FEDERALLY SPONSORED RESEARCH OR DEVELOPMENT

This invention was made with government support under Grant Number R01OH010241 awarded by the Centers for Disease Control—National Institute for Occupational Safety and Health (CDC-NIOSH). The government has certain rights in the invention.

BACKGROUND

The normal wound healing process can be divided into three phases: inflammation, tissue formation, and remodeling. During the tissue formation phase, keratinocytes are responsible for reestablishing the epidermis through a process called epithelialization. Epithelialization has previously been identified as a key parameter of successful wound healing. To complete epithelialization following injury, keratinocytes must attenuate their adhesion to the basal lamina and each other. This permits keratinocytes at the wound edge to migrate, while keratinocytes behind the migrating edge proliferate to ensure sufficient coverage of the wound. Soluble mediators, such as chemokines, are responsible for modulating the tissue formation phase, as keratinocyte expression of chemokine receptors impacts epithelialization.

Chronic wounds are the result of an impaired healing process, and arise following trauma, surgery, and/or disease. Approximately 6.5 million patients within the United States suffer from chronic wounds each year, with associated costs exceeding $25 billion. Epithelialization, a key process in wound healing, is compromised in chronic wounds. As restoration of the wound healing process remains an elusive goal for healthcare professionals, novel therapeutic strategies that focus on the mechanism of tissue repair are desperately needed to treat chronic wounds.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1A:
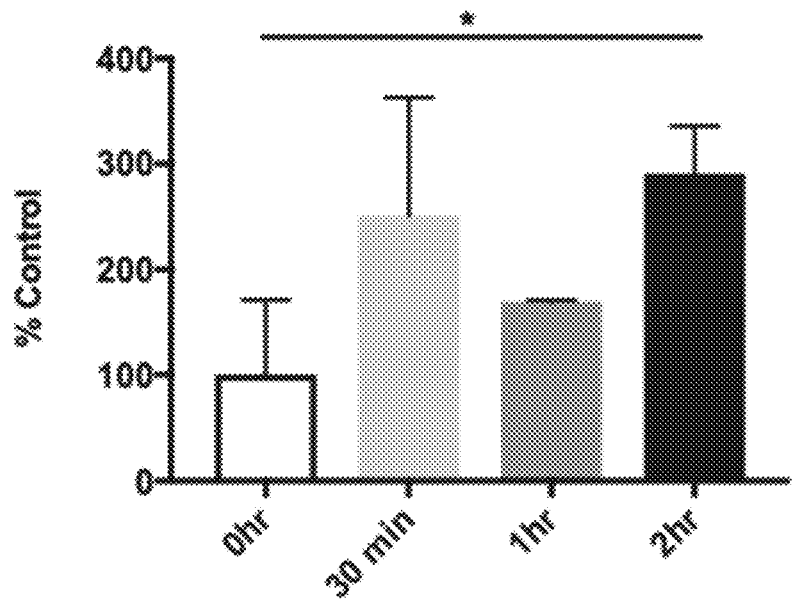
FIG. 1A shows expression of keratinocyte C-C chemokine receptor type-3 (CCR3) following in vitro wounding. HEKn cultures were grown to confluency and wounded. Total cellular RNA was prepared, and expression of CCR3 mRNA (A) was determined by real-time polymerase chain reaction. Bar graph is expressed as mean±SD, $*p<0.05$ versus control (0 hr).

The present disclosure is directed to methods of treating skin wounds in subjects and promoting wound healing. The method comprises administering to a subject (or exposing a keratinocyte to) a C-C chemokine receptor type-3 (CCR3)-inhibitory effective amount of an inhibitory compound ("CCR3 antagonist" or "CCR3 inhibitor") which inhibits the activity of CCR3 or its ligands. The wound may be an acute or chronic wound. The wound may be a wound in a diabetic subject.

The role of keratinocyte CCR3 function during the wound repair process has not previously been evaluated. In the present disclosure, human epidermal keratinocytes were analyzed for CCR3 expression via PCR and histology following wounding. Antagonism of CCR3 with a specific neutralizing antibody was found to promote in vitro wound closure and to increase keratin expression and the percentage of keratinocytes in the G2/M phase. Furthermore, the CCR3-specific ligands Chemokine (C-C motif) ligand 24 (CCL24, a.k.a. eotaxin-2) and Chemokine (C-C motif) ligand 26 (CCL26, a.k.a. eotaxin-3) were found to decrease keratinocyte proliferation. CCR3 blockade was shown to aid the healing of splinted wounds in streptozotocin (STZ)-induced hyperglycemic inbred mice. These results indicate that CCR3 has a pathophysiologic role during the epithelialization phase of cutaneous wound repair, and can be targeted for inhibition for promoting healing of wounds, such as (but not limited to) chronic wounds.

Before further describing various embodiments of the compositions, kits, and methods of the present disclosure in more detail by way of exemplary description, examples, and results, it is to be understood that the present disclosure is not limited in application to the details of methods and compositions as set forth in the following description. The description provided herein is intended for purposes of illustration only and is not intended to be construed in a limiting sense. The inventive concepts of the present disclosure are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure as defined herein. Thus, while the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Use of the word "we" as a pronoun herein refers generally to laboratory personnel or other contributors who assisted in laboratory procedures and data collection and is not intended to represent an inventorship role by said laboratory personnel or other contributors in any subject matter disclosed herein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±20%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, component, step, feature, structure, or characteristic described in connection with the embodiment is included in at least one embodiment. The appearances of the phrase "in one embodiment" in various places in the specification are not necessarily all referring to the same embodiment. Further, all references to one or more embodiments or examples are to be construed as non-limiting to the claims.

When two or more active agents described in the present disclosure, or their equivalents, are administered, they may be used or administered conjointly. As used herein, the terms "conjointly" or "conjoint administration" refer to any form of administration of two or more different biologically-active compounds (i.e., active agents) such that the second compound is administered while the previously administered therapeutic compound is still effective in the body, whereby the two or more compounds are simultaneously active in the patient. For example, the different therapeutic compounds can be administered either in the same formulation, or in separate formulations, either concomitantly (together) or sequentially. When administered sequentially, the different compounds may be administered immediately in succession or administered separately by a suitable duration of time, as long as the active agents function together in a synergistic manner. In certain embodiments, the different therapeutic compounds can be administered within one minute of each other, within 5 minutes of each other, within 10 minutes of each other, within 15 minutes of each other, within 30 minutes or each other, within 45 minutes of each other, within one hour of each other, within two hours of each other, within 3 hours of each other, within 6 hours of each other, within 12 hours of each other, within 24 hours of each other, within 36 hours of each other, within 48 hours of each other, within 72 hours of each other, or more. Thus, an individual who receives such treatment can benefit from a combined effect of the different therapeutic compounds.

The term "pharmaceutically acceptable" refers to compounds and compositions which are suitable for administration to humans and/or animals without undue adverse side effects such as toxicity, irritation, and/or allergic response commensurate with a reasonable benefit/risk ratio.

By "biologically active" is meant the ability of an agent to modify the physiological system of an organism without reference to how the agent ("active agent") has its physiological effects.

As used herein, "pure" or "substantially pure" means an object species is the predominant species present (i.e., it is more abundant on a molar basis than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, and more particularly more than about 85%, more than about 90%, more than about 95%, or more than about 99% of all macromolecular species present in the composition. The term "pure" or "substantially pure" also refers to preparations where the object species is at least about 60% (w/w) pure, or at least about 70% (w/w) pure, or at least about 75% (w/w) pure, or at least about 80% (w/w) pure, or at least about 85% (w/w) pure, or at least about 90% (w/w) pure, or at least about 92% (w/w) pure, or at least about 95% (w/w) pure, or at least about 96% (w/w) pure, or at least about 97% (w/w) pure, or at least about 98% (w/w) pure, or at least about 99% (w/w) pure, or about 100% (w/w) pure.

The terms "subject" and "patient" are used interchangeably herein and will be understood to refer to a warm-blooded animal, particularly a mammal, and more particularly, humans. Animals which fall within the scope of the term "subject" as used herein include, but are not limited to, dogs, cats, rats, mice, guinea pigs, chinchillas, horses, goats, ruminants such as cattle, sheep, swine, poultry such as chickens, geese, ducks, and turkeys, zoo animals, Old and New World monkeys, and non-human primates.

"Treatment" refers to therapeutic treatments, such as for promoting wound healing. "Prevention" refers to prophylactic or preventative treatment measures. The term "treating" refers to administering the composition to a patient for therapeutic purposes such as for promoting wound healing. In at least certain embodiments, the skin wound treatments of the present disclosure cause an increase in the rate of contraction of the wound as compared to a rate of contraction of the skin wound that would occur without the treatment.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent (e.g., a CCR3 inhibitor) which is sufficient to exhibit a detectable therapeutic effect without excessive adverse side effects (such as toxicity, irritation, and allergic response) commensurate with a reasonable benefit/risk ratio when used in the manner of the inventive concepts. The therapeutic effect may include, for example but not by way of limitation, a partial or complete healing (e.g., closure or contraction) of a wound. The effective amount for a patient will depend upon the type of patient, the patient's size and health, the nature and severity of the wound to be treated, the method of administration, the duration of treatment, the nature of concurrent therapy (if any), the specific formulations employed, and the like. The effective amount for a given situation can be determined by one of ordinary skill in the art based on the information provided herein.

The term "ameliorate" means a detectable or measurable improvement in a subject's condition, disease, or symptom thereof. A detectable or measurable improvement includes a subjective or objective decrease, reduction, inhibition, closure, suppression, limit, or control in the occurrence, frequency, severity, progression, or duration of the condition or disease, or an improvement in a symptom or an underlying cause or a consequence of the disease, or a reversal of the disease. A successful treatment outcome can lead to a "therapeutic effect" or "benefit" of completely or partially decreasing, reducing, inhibiting, suppressing, limiting, controlling, or preventing the occurrence, frequency, severity, progression, or duration of a disease or condition, or consequences of the disease or condition, such as (but not limited to) a wound, in a subject.

A decrease or reduction in the worsening of a disease or condition, such as stabilizing the condition or disease, such as a wound, is also a successful treatment outcome. A therapeutic benefit therefore need not be complete ablation or reversal of the disease or condition, or of any one of, or most, or all adverse symptoms, complications, consequences, or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.), such as partial closure of a wound. Effectiveness of a method or use, such as a treatment that provides a potential therapeutic benefit or improvement of a condition or disease, can be ascertained by various methods, measurements, and testing assays.

The terms "CCR3 antagonist" and "CCR3 inhibitor" may be used interchangeably herein and are intended to refer to compounds which antagonize or inhibit CCR3 or CCR3 ligands such that the activity of CCR3 or the CCR3 ligand is reduced or decreased.

Certain non-limiting embodiments of the present disclosure are directed to a method of treating a skin wound in a subject, comprising administering to the subject at least one inhibitor selected from the group consisting of inhibitors of CCR3 and inhibitors of a CCR3 ligand, thereby causing increased activity of keratinocytes adjacent the skin wound. In this method, epithelialization of the skin wound is increased. In addition, the increased activity of keratinocytes may be defined as at least one of (1) increased proliferation of the keratinocytes and (2) increased migration of the keratinocytes adjacent the skin wound.

Certain non-limiting embodiments of the present disclosure are directed to a method of treating a skin wound, comprising administering to a subject in need of such therapy at least one inhibitor selected from the group consisting of inhibitors of CCR3 and inhibitors of a CCR3 ligand. The at least one inhibitor is administered to the subject in an amount effective to cause increased proliferation of keratinocytes adjacent the skin wound, thereby enhancing epithelialization of the skin wound.

In a particular (but non-limiting) embodiment, the increased proliferation of keratinocytes occurs at a leading edge of the skin wound. Treatment of the skin wound causes an increase in the rate of closure of the wound as compared to a rate of closure of the skin wound that would occur without the treatment.

Certain non-limiting embodiments of the present disclosure are directed to a method of treating a skin wound, comprising administering to a subject in need of such therapy at least one inhibitor selected from the group consisting of inhibitors of CCR3 and inhibitors of a CCR3 ligand. The at least one inhibitor is administered to the subject in an amount effective to cause increased migration of keratinocytes adjacent the skin wound, thereby enhancing epithelialization of the skin wound.

In a particular (but non-limiting) embodiment, the increased migration of keratinocytes occurs at a leading edge of the skin wound. Treatment of the skin wound causes an increase in the rate of closure of the wound as compared to a rate of closure of the skin wound that would occur without the treatment.

Certain non-limiting embodiments of the present disclosure are directed to a method of promoting wound healing in a subject having a wound, comprising exposing a keratinocyte of the wound to a CCR3-inhibitory effective amount of at least one inhibitor which inhibits the activity of CCR3, wherein the compound is selected from the group consisting of inhibitors of CCR3 and inhibitors of a CCR3 ligand. Treatment of the skin wound causes an increase in the rate of closure of the wound as compared to a rate of closure of the skin wound that would occur without the treatment.

In certain particular (but non-limiting) embodiments, the skin wound treated in any of the methods disclosed above or otherwise contemplated herein is an acute wound.

In certain particular (but non-limiting) embodiments, the skin wound treated in any of the methods disclosed above or otherwise contemplated herein is a chronic wound (such as, but not limited to, a diabetic wound).

In particular (but non-limiting) embodiments, the at least one inhibitor utilized in any of the methods disclosed above or otherwise contemplated herein can include an antibody and/or antibody fragment which specifically binds to CCR3 or to the CCR3 ligand.

In particular (but non-limiting) embodiments, the at least one inhibitor utilized in any of the methods disclosed above or otherwise contemplated herein can include an siRNA which inhibits expression of CCR3.

In particular (but non-limiting) embodiments, the at least one inhibitor utilized in any of the methods disclosed above or otherwise contemplated herein can include a small molecule or any other compound capable of inhibiting the activity of CCR3 as described herein.

Any compound which inhibits the activity of CCR3, directly or indirectly, may be used in the presently disclosed methods of treatment. Such compounds include inhibitory molecules which bind directly to CCR3; antibodies (or antibody fragments) which bind to CCR3; compounds or antibodies (or antibody fragments) which bind to the natural ligands of CCR3 (e.g., eotaxin (CCL11), eotaxin-2 (CCL24), and eotaxin-3 (CCL26)); RNA, DNA, or RNA/DNA aptamers which specifically bind CCR3 or its ligands; and siRNA or anti-sense oligonucleotides which inhibit the expression of CCR3 or its ligands.

Numerous "small molecule" inhibitors for CCR3 have been developed and can be used herein. In one aspect, the CCR3 inhibitor can be an organic molecule having a molecular weight less than 1000. In another aspect, the CCR3 inhibitor can be an organic molecule having a molecular weight less than 500. The CCR3 receptor inhibitors include piperidine derivatives, piperidine amides, and piperidine compounds such as (but not limited to) those described in U.S. Pat. Nos. 6,984,651 and 6,903,115, and U.S. published patent applications US 2005/0176708, US 2005/0182094, and US 2005/0182095; heterocyclic piperidines such as (but not limited to) those described in U.S. Pat. No. 6,759,411; diphenyl-piperidine derivatives such as (but not limited to) those described in U.S. Pat. No. 6,566,376; 2,5-substituted pyrimidine derivatives such as (but not limited to) those described in U.S. Pat. No. 6,984,643; piperizinones such as (but not limited to) those described in U.S. Pat. No. 6,974,869; bicyclic and tricyclic amines such as (but not limited to) those described in U.S. Pat. No. 6,960,666; N-ureidoalkyl-piperidines such as (but not limited to) those described in U.S. Pat. Nos. 6,949,546; 6,919,368; 6,906,066; 6,897,234; 6,875,776; 6,780,857; 6,627,629; 6,521,592; and 6,331,541; bicyclic diamines such as (but not limited to) those described in U.S. Pat. No. 6,821,964; benzylcycloalkyl amines such as (but not limited to) those described in U.S. Pat. No. 6,864,380; 2-substituted-4-nitrogen heterocycles such as (but not limited to) those described in U.S. Pat. No. 6,706,735; ureido derivatives of poly-4-amino-2-carboxy-1-methylpyrrole compounds; bicyclic and bridged nitrogen heterocycles such as (but not limited to) those described in U.S. published patent application US 2005/0234034; azetidine derivatives such as (but not limited to) those described in U.S. published patent application US 2005/0222118; substituted fused bicyclic amines such as (but not limited to) those described in U.S. published patent application US 2005/0197373; substituted spiro azabicyclics such as (but not limited to) those described in U.S. published patent application US 2005/0197325; piperidine-substituted indoles or heteroderivatives thereof such as (but not limited to) those described in U.S. published patent application US 2005/0153979; piperidinyl and piperazinyl compounds substituted with bicyclo-heterocyclylalkyl groups such as (but not limited to) those described in U.S. published patent application US 2005/0090504; arylsulfonamide derivatives such as (but not limited to) those described in U.S. published patent application US 2005/0070582; 1-phenyl-1,2-diaminoethane derivatives such as (but not limited to) those described in U.S. published patent application US 2004/0063779; N-{[2S]-4-(3,4-dichlorobenzyl)morpholin-2-yl}methyl)-N'[(2-methyl-2H-tet-raazol-5-yl)methyl]urea (see, e.g., Nakamura et al., Immunol Res., 33:213-222, 2006; N-{43R)-1-[(6-fluoro-2-naphthyl)methyl]pyrrolidin-3-yl}-2-{1-[(3-methyl-1-oxidopyridin-2-yl)carbonyl]piperidin-4-ylidene}acetamide (see, e.g., Suzuki et al., Biochem. Biophys. Res. Commun., 339:1217-1223, 2006); N-{(3R)-1-[(6-fluoro-2-naphthyl)methyl]pyrrolidin-3 -yl}-2-{1-[(5-hydroxy-3-methylpyridin-2-yl)carbonyl]piperidin-4-ylidene}acetamide hemifumarate (see, e.g., Morokata et al., J. Pharmacol. Exp. Ther., Dec. 9, 2005 [Epub ahead of print]); bipiperidine amide antagonists of CCR3 such as (but not limited to) those described in Ting et al., Bioorg. Med. Chem. Lett., 15:3020-3023, 2005; (S)-methyl-2-naphthoy-lamino-3-(4-nitrophenyl) propionate (see, e.g., Beasley et al., J. Allergy Clin. Immunol., 105: S466-S472, 2000); and the CCR3 antagonist compounds described in Fryer et al. (J. Clin. Invest., 116:228-236, 2006).

Particular (but non-limiting) examples of small molecule CCR3 antagonists that can be used in non-limiting embodiments of the present disclosure are shown in FIGS. 6-23.

Additional compounds for inhibiting CCR3 include RNA, DNA, or RNA/DNA aptamers directed against CCR3 or its ligands. Exemplary methods for making aptamers are described in (for example, but not by way of limitation) U.S. Pat. Nos. 5,270,163; 5,840,867; 6,180,348; and 6,699,843.

Additional compounds for inhibiting the CCR3 receptor include anti-sense oligonucleotides or siRNAs directed against CCR3 or its ligands, including the anti-sense oligonucleotides directed against CCR3 such as (but not limited to) those described in U.S. Pat. No. 6,822,087. Introduction of siRNAs into cells may be by transfection with expression vectors, by transfection with synthetic dsRNA, or by any other appropriate method. Expression vectors which can be used to deliver siRNA include retroviral, adenoviral, and lentiviral vectors. The expression vector includes a sequence which codes for a portion of the target gene (genes for CCR3 receptor or its ligands) which is to be silenced. The target gene sequence is designed such that, upon transcription in the transfected host, the target RNA sequence forms a hairpin structure due to the presence of self-complementary bases. Processing within the cell removes the loop resulting in formation of a siRNA duplex. The double stranded RNA sequence may be in a range of 12-30 nucleotide bases in length for example. The expression vectors may include one or more promoter regions to enhance synthesis of the target gene sequence. Promoters which can be used include CMV promoter, SV40 promoter, promoter of mouse U6 gene, and promoter of human H1 gene. Synthetic dsRNA may also be introduced into cells to provide gene silencing by siRNA. The synthetic dsRNAs are generally about 15 to about 30 base pairs in length, e g., about 19 to about 25 base pairs in length. Synthetic dsRNAs can be introduced into cells by injection, by complexing with agents such as cationic lipids, by use of a gene gun, or by any other appropriate method.

Additional compounds for inhibiting CCR3 include antibodies which specifically bind the CCR3 or its ligands. Non-limiting examples of antibodies which specifically bind and inhibit the CCR3 are described in U.S. Pat. Nos. 6,806,061 and 6,207,155, and in U.S. published patent applications US 2005/0191702, US 2005/0069955, and US 2002/0147312. Non-limiting examples of antibodies which specifically bind and inhibit eotaxin and eotaxin-2 are described in U.S. Pat. Nos. 6,946,546 and 6,635,251, and in U.S. published patent applications US 2004/0191255 and US 2004/0014132.

The antibodies of the present disclosure can be polyclonal or monoclonal, and the term antibody is intended to encompass both polyclonal and monoclonal antibodies. Antibodies of the present disclosure can be raised against an appropriate immunogen, including proteins or polypeptides of the present disclosure, such as (but not limited to) isolated and/or recombinant mammalian CCR3, eotaxin, eotaxin-2 or eotaxin-3 protein, or a portion thereof, or synthetic molecules, such as synthetic peptides. Non-limiting examples of antibodies which can be used in the methods of the present disclosure include those shown in Tables 1 and 2, as well as functional fragments thereof.

TABLE 1

Anti-Human CCR3 Monoclonal Antibodies

| Number | Identity | Source |
|---|---|---|
| MAB155 | Monoclonal Rat IgG2A Clone # 61828 | R&D systems, Minneapolis, MN |
| 711263 | CCR3 Recombinant Polyclonal Antibody (23HCLC) | ThermoFisher, Waltham, MA |
| 5E8-G9-B4 | CD193 (CCR3) Monoclonal Antibody (eBio5E8-G9-B4 (5E8-G9-B4)), eBioscience ™ | ThermoFisher/eBioscience |
| EPR23893-40 | Rabbit monoclonal to CCR3 | Abcam, Cambridge, UK |
| Y31 | Rabbit monoclonal to CCR3 | Abcam |
| 5E8 | Mouse monoclonal to CCR3 | Abcam |
| 83101 | Anti-CCR3 Hybridoma [83101] (CSC-S138) | Creative Diagnostics, Shirley, NY |
| 7B11 | Anti-CCR3 Hybridoma [7B11] (CSC-S139) | Creative Diagnostics |

TABLE 2

Anti-Human CCR3 Polyclonal Antibodies

| Number | Identity | Source |
|---|---|---|
| PA5-117846 | CCR3 Polyclonal Antibody (rabbit) | ThermoFisher/Invitrogen |
| PAS-19859 | CCR3 Polyclonal Antibody (rabbit) | ThermoFisher/Invitrogen |
| PA5-27168 | CCR3 Polyclonal Antibody (rabbit) | ThermoFisher/Invitrogen |
| 22351-1-AP | CCR3 Polyclonal Antibody (rabbit) | ThermoFisher/Proteintech |
| ab36827 | CCR3 Polyclonal Antibody (rabbit) | Abcam |
| LS-A101031 | CCR3 Polyclonal Antibody (rabbit) | LSBio, Seattle, WA |

Preparation of immunizing antigen and production of polyclonal and monoclonal antibodies can be performed using any suitable techniques known in the art or otherwise contemplated herein. A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; etc.). Generally, a hybridoma is produced by fusing a suitable immortal cell line (e.g., a myeloma cell line such as SP2/0) with antibody producing cells. The antibody producing cell, such as those of the spleen or lymph nodes, are obtained from animals immunized with the antigen of interest. The fused cells (hybridomas) are isolated using selective culture conditions and cloned by limiting dilution. Cells which produce antibodies with the desired specificity are selected by a suitable assay (e.g., ELISA).

Single chain antibodies, and chimeric, humanized, or primatized (CDR-grafted) antibodies (as well as chimeric or CDR-grafted single chain antibodies) comprising portions derived from different species, are also encompassed by the present disclosure and the term "antibody" as used herein. The various portions of these antibodies can be joined together chemically by conventional techniques or can be prepared as a contiguous protein using genetic engineering techniques. For example (but not by way of limitation), nucleic acids encoding a chimeric or humanized chain can be expressed to produce a contiguous protein. See, e.g., Cabilly et al., U.S. Pat. No. 4,816,567; Cabilly et al., European Patent No. 0,125,023. B1; Boss et al., U.S. Pat. No. 4,816,397; Boss et al., European Patent No. 0,120,694 B1; Neuberger, M. S. et al., international patent application publication WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al. (BioTechnology, 10: 1455-1460 (1992)), regarding primatized antibody, and Ladner et al. (U.S. Pat. No. 4,946,778) and Bird, R. E. et al. (Science, 242: 423-426 (1988)) regarding single chain antibodies.

In addition, functional fragments of antibodies, including fragments of chimeric, humanized, primatized, or single chain antibodies, can also be produced. Functional fragments of foregoing antibodies retain at least one binding function and/or modulation function of the full-length antibody from which they are derived. For example, antibody fragments capable of binding to a mammalian CCR3 or its ligands, or a portion thereof, including, but not limited to, Fv, Fab, Fab', and F(ab')$_2$ fragments are encompassed by the present disclosure. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CHi domain and hinge region of the heavy chain.

The term "wound" as used herein in reference to the skin refers to a break in the continuity of the skin (or other external surface). Wounds are generally further defined as "acute" or "chronic." An acute wound may be caused by an external force, trauma, or injury. Acute wounds include incisions, excisions (e.g., of extensive skin cancer), tears, punctures, cuts, lacerations, avulsions, necroses, burns from heat or radiation, abrasions, aseptic wounds, contusions, non-penetrating wounds (i.e. wounds in which there is no disruption of the skin but there is injury to underlying structures), open wounds, penetrating wounds, perforating wounds, puncture wounds, septic wounds, sores, and subcutaneous wounds, and the wounds can be caused accidentally or purposefully (e.g., by surgery), deep fungal and bacterial infections, vasculitis, scleroderma, pemphigus, and toxic epidermal necrolysis. Examples of sores include (for example but not by way of limitation) pressure sores (e.g., bed sores), cancer sores, chrome sores, and cold sores. The wound may be located internally or externally in/on a subject. A chronic wound is generally defined as a wound which is unhealed after at least three weeks to three months, or a wound that does not completely heal, or that has failed to proceed through an orderly and timely process to produce sustained anatomic and functional integrity through the repair process. A chronic wound may be derived from an acute wound which has become infected, causing the wound to become inflamed and thereby interrupting the normal healing process. In certain cases, chronic wounds are referred to herein as ulcers. In general, an ulcer is defined as a breakdown or gradual disturbance in the skin (or other external surface) tissue caused by an underlying (internal) etiology or pathology.

The wound may also be due to a disorder (such as, but not limited to, diabetes), an infectious lesion, surgery, or a puncture. The wound may be due to destructive wound inflammation, delayed or impaired healing, or disturbed tissue regeneration. The term "accelerating wound healing" or "acceleration of wound healing" refers to the increase in the rate of healing, e.g., a reduction in time until complete wound closure occurs or a reduction in time until a % reduction in wound area occurs.

The term "ulcer" refers a site of damage to the skin or mucous membrane that is often characterized by the formation of pus, death of tissue (necrosis), and is accompanied by an inflammatory reaction. Ulcers are frequently chronic wounds. A "diabetic wound" is a wound that is associated with diabetes. A "diabetic ulcer" is an ulcer that is associated with diabetes. A "chronic wound" refers a wound that has not healed within three months. Chronic wounds include, but are not limited to, e.g., arterial ulcers, diabetic ulcers, pressure ulcers or bed sores, and venous ulcers. An acute wound can develop into a chronic wound. A "dermal wound" refers to a lesion in one or more layers of skin of a subject, e.g., wherein the lesion comprises one or more apoptotic dermal cells and/or one or more necrotic dermal cells. The term "dermal wound" shall be taken to include a wound that affects an epidermal layer of a subject and/or a dermal layer of a subject and/or a hypodermal layer of a subject. The term "healing" in the context of the present disclosure is a promotion or acceleration of the time from when the compound is administered until significant or complete wound closure (full wound contraction). A non-diabetic wound is a wound that occurs in a subject who does not have diabetes.

Wounds may be caused by, or may become chronic due to, ischemia. Ischemia is caused by limited blood supply to a wound site causing a shortage of oxygen and other necessary blood-borne products required by the tissue due to increased metabolic costs of healing. Peripheral vascular disease or disruption is a common cause of ischemic wounds. Individuals with poor peripheral circulation are at high risk for developing ischemic chronic wounds. Other medical conditions associated with ischemic wounds include diabetes mellitus, renal failure, hypertension, lymphedema, inflammatory diseases such as vasculitis or lupus, and current or past tobacco use. Ischemic wounds thus refer to wounds to which the flow of blood has been obstructed, restricted, or otherwise impaired, such that the wound site is deprived of oxygen and nutrients. Damaged tissue deprived of adequate blood flow has a decreased ability to heal, and as such predisposes individuals to the development of chronic wounds.

In certain embodiments, the compounds and compositions disclosed herein may be used to treat and promote healing of wounds in subjects who are otherwise healthy, i.e., subjects who do not have chronic conditions which impair wound healing (such as, but not limited to, diabetes). Examples of such wounds in otherwise healthy subjects include, but are not limited to, surface wounds such as lacerations, abrasions, avulsions, incisions, and amputations, and other wounds described above or elsewhere herein. In certain embodiments, the compounds and compositions are used to enhance and/or promote healing of acute wounds of a non-diabetic nature (e.g., lacerations, abrasions, avulsions, incisions, amputations, and burns).

In certain embodiments, the compounds and compositions disclosed herein may be used to treat and promote healing of chronic or non-healing wounds such as (but not limited to) diabetic wounds and ulcers (for example of the legs and feet)

in subjects having diabetes, or wounds due to peripheral vascular disease or cardiovascular disease in subjects who have chronic conditions which impair wound healing. Thus, in certain embodiments, the compounds and compositions of the present disclosure are used to enhance and/or promote healing of chronic wounds.

As noted elsewhere herein, a successful treatment does not require complete healing or closure of a wound but may comprise an amelioration of the wound, for example a partial closure of the wound or partial epithelialization of the wound. The compounds and compositions in certain embodiments may be used as treatments to enhance acceptance of grafts such as skin grafts.

The active agents described herein may be used in combination with each other, or in combination with other therapeutic drugs given to treat a particular condition, such as an acute or chronic wound.

In certain non-limiting embodiments, the dosage of the CCR3 inhibitor administered to a subject could be in a range of from about 1 µg per kg of subject body mass to about 1000 mg/kg, or in a range of from about 5 µg/kg to about 500 mg/kg, or in a range of from about 10 µg/kg to about 300 mg/kg, or in a range of from about 25 µg/kg to about 250 mg/kg, or in a range of from about 50 µg/kg to about 250 mg/kg, or in a range of from about 75 µg/kg to about 250 mg/kg, or in a range of from about 100 µg/kg to about 250 mg/kg, or in a range of from about 200 µg/kg to about 250 mg/kg, or in a range of from about 300 µg/kg to about 250 mg/kg, or in a range of from about 400 µg/kg to about 250 mg/kg, or in a range of from about 500 µg/kg to about 250 mg/kg, or in a range of from about 600 µg/kg to about 250 mg/kg, or in a range of from about 700 µg/kg to about 250 mg/kg, or in a range of from about 800 µg/kg to about 250 mg/kg, or in a range of from about 900 µg/kg to about 250 mg/kg, or in a range of from about 1 mg/kg to about 200 mg/kg, or in a range of from about 1 mg/kg to about 150 mg/kg, or in a range of from about 2 mg/kg to about 100 mg/kg, or in a range of from about 5 mg/kg to about 100 mg/kg, or in a range of from about 10 mg/kg to about 100 mg/kg, or in a range of from about 25 mg per kg to about 75 mg/kg.

The one or more CCR3 inhibitors (alone, or used conjointly with another therapeutic) can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method of the present disclosure, the composition is provided in an IV infusion. Administration of the compounds used in the pharmaceutical composition or to practice the method of the present disclosure can be carried out in a variety of conventional ways, such as, but not limited to, topically, orally, by inhalation (e.g., intrabronchial, intranasal or oral inhalation, intranasal drops), rectally, or by cutaneous, subcutaneous, intraperitoneal, or parenteral (e.g., intravenous, intraarterial, intramuscular, subcutaneous injection) injection. Oral formulations may be formulated such that the compounds pass through a portion of the digestive system before being released, for example it may not be released until reaching the small intestine, or the colon. When the active agent is delivered by inhalation, it may be delivered via a soft mist nebulizer (e.g., a jet, ultrasonic, or vibrating-mesh nebulizer), a pressurized metered-dose inhaler (MDI), or a dry powder inhaler (DPI), or by any other suitable means, e.g., via a catheter inserted directly into the lung, or via a ventilator when a patient himself or herself is unable to inhale voluntarily.

As noted above, in certain embodiments, the compositions of the present disclosures may be applied topically to an external or internal wound. The treated wounds may be acute wounds, such as abrasions, lacerations, punctures, avulsions and incisions, or other acute wounds as described herein, or may be chronic wounds, such as non-diabetic chronic wounds, or diabetic chronic wounds including but not limited to diabetic foot and leg ulcers, venous leg ulcers, pressure ulcers (e.g., bed sores), wounds due to arterial insufficiency, wounds caused by burns or radiation, and chronic surgical wounds (e.g., due to abdominal surgery), or other chronic wounds as described herein.

In certain embodiments, the methods of the present disclosure include topical, transdermal, sub-dermal, enteral, parental, or intravenous administration of an active agent (one or more CCR3 inhibitors). For example (but not by way of limitation), topical administration of the active agent may comprise the administration of a cream, gel, ointment, spray, lip-balm, balm, emulsion, liposome, liquid crystal preparation or lotion, or any combination thereof. In one embodiment, administration comprises an at least once a day administration for one or more days (e.g., about 1 to about 30 days) until at least one symptom of the inflammatory disease or condition is alleviated. In another embodiment, administration comprises an at least twice a day administration for one or more days (e.g., about 1 to about 30 days) until at least one symptom of the condition is alleviated. In another embodiment, administration comprises an at least about 3 to about 6 times per day administration for one or more days (e.g., about 1 to about 30 days) until at least one symptom of the condition is alleviated.

The composition for topical or internal application may be provided in any suitable solid, semi-solid, or liquid form. In certain embodiments, the topical composition may be provided in or be disposed in a carrier(s) or vehicle(s) such as, for example (but not by way of limitation), creams, pastes, gums, lotions, gels, foams, ointments, emulsions, suspensions, aqueous solutions, powders, lyophilized powders, solutions, granules, foams, drops, eye drops, adhesives, sutures, aerosols, sprays, sticks, soaps, bars of soap, balms, body washes, rinses, tinctures, gel beads, gauzes, wound dressings, bandages, cloths, towelettes, stents, and sponges. Non-limiting examples of formulations of such carriers and vehicles include, but are not limited to, those shown in "*Remington, The Science and Practice of Pharmacy,*" 22nd ed., 2012, edited by Loyd V. Allen, Jr.

Creams are emulsions of water in oil (w/o), or oil in water (o/w). O/w creams spread easily and do not leave the skin greasy and sticky. W/o creams tend to be more greasy and more emollient. Ointments are semi-solid preparations of hydrocarbons and the strong emollient effect makes it useful in cases of dry skin. The occlusive effect enhances penetration of the active agent and improves efficacy. Pastes are mixtures of powder and ointment. The addition of the powder improves porosity thus breathability. The addition of the powder to the ointment also increases consistency so the preparation is more difficult to rub off or contact non-affected areas of the skin. Lotions are liquid preparations in which inert or active medications are suspended or dissolved. For example, an o/w emulsion with a high water content gives the preparation a liquid consistency of a lotion. Most lotions are aqueous of hydroalcoholic systems wherein small amounts of alcohol are added to aid in solubilization of the active agent and to hasten evaporation of the solvent from the skin surface. Gels are transparent preparations containing cellulose ethers or carbomer in water, or a water-alcohol mixture. Gels liquefy on contact with the skin, dry, and leave a thin film of active medication.

A person with ordinary skill in the art will be capable of determining the effective amount of the composition needed for a particular treatment. Such amount may depend on the strength of the composition or extent of the wound to be treated. Although a person with ordinary skill in the art will know how to select a treatment regimen for a specific condition. In a non-limiting example, a dosage of the composition comprising about 0.001 mg to about 10 mg of the active agent per ml may be applied 1 to 2 to 3 to 4 to 5 to 6 times per day or more to the affected area. It is foreseeable in some embodiments that the composition is administered over a period of time. The composition may be applied for a day, multiple days, a week, multiple weeks, a month, or even multiple months in certain circumstances. Alternatively, the composition may be applied only once when the skin condition is mild.

In certain non-limiting embodiments, the composition may comprise the active agents in a concentration of, but is not limited to, a range of from about 0.0001 M to about 1 M, for example, or a range of from about 0.001 M to about 0.1 M. The composition may comprise about 0.01 to about 1000 milligrams of the active agents per ml of carrier or vehicle with which the active agents are combined in a composition or mixture. The composition may comprise about 1 wt % to about 90 wt % (or about 1 mass % to about 90 mass %) of one or more shikimate analogues and about 10 wt % to about 99 wt % (or about 10 mass % to about 99 mass %) of one or more secondary compounds (where "wt %" is defined as the percentage by weight of a particular compound in a solid or liquid composition, and "mass %" is defined as the percentage by mass of a particular compound in a solid or liquid composition).

The topical compositions may further comprise ingredients such as (but not limited to) propylene glycol, sodium stearate, glycerin, a surfactant (e.g., sodium laurate, sodium laureth sulfate, and/or sodium lauryl sulfate), and water, and optionally, sorbitol, sodium chloride, stearic acid, lauric acid, aloe vera leaf extract, pentasodium penetrate, and/or tetrasodium etidronate.

The topical compositions may be formulated with liquid or solid emollients, solvents, thickeners, or humectants. Emollients include, but are not limited to, stearyl alcohol, mink oil, cetyl alcohol, oleyl alcohol, isopropyl laurate, polyethylene glycol, olive oil, petroleum jelly, palmitic acid, oleic acid, and myristyl myristate. Emollients may also include natural butters extracted from various plants, trees, roots, or seeds. Examples of such butters include, but are not limited to, shea butter, cocoa butter, avocado butter, aloe butter, coffee butter, mango butter, or combination thereof.

Suitable materials which may be used in the compositions as carriers or vehicles or secondary compounds or solvents include, but are not limited to, propylene glycol, ethyl alcohol, isopropanol, acetone, diethylene glycol, ethylene glycol, dimethyl sulfoxide, and dimethyl formamide. Suitable humectants include, but are not limited to, acetyl arginine, algae extract, Aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed wheat protein/polyethylene glycol-20 acetate copolymer, hydroxypropyltrimonium hyaluronate, inositol, lactitol, maltitol, maltose, mannitol, mannose, methoxypolyethylene glycol, myristamidobutyl guanidine acetate, polyglyceryl sorbitol, potassium pyrrolidone carboxylic acid (PCA), propylene glycol (PGA), sodium pyrrolidone carboxylic acid (PCA), sorbitol, and sucrose. Other humectants may be used for yet additional embodiments of the compositions of the present disclosure.

Suitable thickeners include, but are not limited to, polysaccharides, in particular xanthan gum, guar-guar, agar-agar, alginates, carboxymethylcellulose, relatively high molecular weight polyethylene glycol mono- and diesters of fatty acids, polyacrylates, polyvinyl alcohol and polyvinylpyrrolidone, surfactants such as, for example, ethoxylated fatty acid glycerides, esters of fatty acids with polyols such as, for example, pentaerythritol or trimethylpropane, fatty alcohol ethoxylates or alkyl oligoglucosides, and electrolytes, such as sodium chloride and ammonium chloride.

The topical compositions may further comprise one or more penetrants, compounds facilitating penetration of active ingredients into the skin of a patient. Non-limiting examples of suitable penetrants include isopropanol, polyoxyethylene ethers, terpenes, cis-fatty acids (oleic acid, palmitoleic acid), acetone, laurocapram dimethyl sulfoxide, 2-pyrrolidone, oleyl alcohol, glyceryl-3-stearate, cholesterol, myristic acid isopropyl ester, and propylene glycol. Additionally, the compositions may include surfactants or emulsifiers for forming emulsions. Either a water-in-oil or oil-in-water emulsion may be formulated. Examples of suitable emulsifiers include, but are not limited to, stearic acid, cetyl alcohol, PEG-100, stearate and glyceryl stearate, cetearyl glucoside, polysorbate 20, methylcellulose, sodium carboxymethylcellulose, glycerin, bentonite, ceteareth-20, cetyl alcohol, cetearyl alcohol, lanolin alcohol, riconyl alcohol, self-emulsifying wax (e.g., Lipowax P), cetyl palmitate, stearyl alcohol, lecithin, hydrogenated lecithin, steareth-2, steareth-20, and polyglyceryl-2 stearate.

The active agents of the present disclosure can be combined with commercially available wound repairing or healing dressings, such as, for example (but not by way of limitation), a sodium chloride dressing (e.g., Mesalt™ by Molnlycke Health Care AB, Goteborg, Sweden), a silver antimicrobial dressing (e.g., SilvaSorb™ by AcryMed, Inc., Portland, OR and Acticoat™ or Acticoat™ 7 by Smith & Nephew, Inc., Largo, FL), a silver impregnated antimicrobial dressing (e.g., Aquacel™ by ConvaTec Limited, Division of E. R. Squibb and Sons, Inc., Princeton, N.J. and Maxorb™ by Medline Industries, Inc., Mundelein, IL), a sodium alginate silver oxide dressing, optionally containing sustained-release polymers that dissolve in water releasing silver ions into the wound (e.g., Argiaes™ Powder by Medline Industries, Inc., Mundelein, IL), a hydrocolloid dressing, optionally containing an inner wound contact layer of hydrocolloids contained within an adhesive polymer matrix and an outer layer of polyurethane film (e.g., SignaDress™ DuoDerm™ by ConvaTec Limited, Division of E. R. Squibb and Sons, Inc., Princeton; N.J.), a collagen and/or calcium alginate dressing (e.g., Fibracol™ by Johnson and Johnson Medical, Skipton, United Kingdom and AlgiSite™ M by Smith & Nephew, Inc., Largo, FL), a dressing layer containing soft silicone (e.g., Mepitel™ by Molnlycke Health Care AB, Goteborg, Sweden), a dressing containing polyhexamethylene biguanide and/or cellulose (e.g., XCell™ by XYLOS Corporation, Langhorne, PA), a dressing containing hyaluronic acid or an ester of hyaluronic acid (e.g., Hyaff™, Hyalofill™ F, or Hyalofill™ R by ConvaTec Limited, Division of E. R. Squibb and Sons, Inc., Princeton, NJ), a dressing made of sponge, optionally containing hydrofera bacteriostatic polyvinyl alcohol sponge (e.g., Hydrofera Blue™ by Hydrofera™, Willimantic, CT), and/or a dressing or pad containing spherical hydrophilic beads of cadexomer, optionally containing iodine and/or polyethylene glycol (e.g., Iodoflex™ Pad by Healthpoint, Ltd., San Antonio, TX).

The active agents of the present disclosure can further be combined with commercially available wound repairing or healing ointments, such as, for example (but not by way of limitation), an ointment containing papain, which is derived from papaya (e.g., Panafil™ or Accuzyme™ by Healthpoint, Ltd., Fort Worth, TX).

The active agents of the present disclosure can also be combined with commercially available wound repairing or healing gels, such as, for example (but not by way of limitation), a sodium chloride gel (e.g., Hypergel™ by Molnlycke Health Care AB, Goteborg, Sweden); and/or gels containing one or more of the following ingredients water, glycerin, glycereth-7, polyvinylpyrrolidone, carbomer, triethanolamine, EDTA, propylene glycol, diazolidinyl urea, methylparaben, and propylparaben, such as found together in 3M Tegagel™ Hydrogel Wound Filler (3M Heath Care, St. Paul, MN).

The active agents of the present disclosure can further be combined with commercially available wound repairing or healing sprays, such as, for example (but not by way of limitation), a spray containing papain (e.g., Panafil™ Spray by Healthpoint, Ltd., Fort Worth, TX).

In certain embodiments, when the composition of the present disclosure is in the form of a composition for external (topical) application to a wound, the dosage thereof to an adult may be in a range of from about 1 μg to about 1000 μg, or more particularly, in a range of from about 10 μg to about 500 μg, as the amount of active agent(s) per dosage. The frequency of administration of the composition is determined by the attending physician or health provider.

In some formulations, such as in aerosol form, the composition may also include a propellant. For example (but not by way of limitation), hydrofluoroalkanes (HFA) such as either HFA 134a (1,1,1,2-tetrafluoroethane) or HFA 227 (1,1,1,2,3,3,3-heptafluoropropane) or combinations of the two, may be used since they are widely used in medical applications. Other suitable propellants include, but are not limited to, mixtures of volatile hydrocarbons, typically propane, n-butane and isobutane, dimethyl ether (DME), methylethyl ether, nitrous oxide, and carbon dioxide. Those skilled in the art will readily appreciate that emollients, solvents, thickeners, humectants, penetrants, surfactants or emulsifiers, and propellants, other than those listed may also be employed.

When a therapeutically effective amount of the composition(s) is administered orally, it may be in the form of a solid or liquid preparation such as (but not by way of limitation) capsules, pills, tablets, lozenges, melts, powders, suspensions, solutions, elixirs or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition(s) may contain a solid carrier, such as a gelatin or an adjuvant. The tablet, capsule, and powder may contain from about 0.05 to about 95% of the active agent by dry weight. When administered in liquid form, a liquid carrier such as (but not limited to) water, petroleum, oils of animal or plant origin such as peanut oil, mineral oil, soybean oil, or sesame oil, or synthetic oils may be added. The liquid form of the pharmaceutical composition(s) may further contain physiological saline solution, dextrose or other saccharide solution, or glycols such as ethylene glycol, propylene glycol, or polyethylene glycol. When administered in liquid form, the pharmaceutical composition(s) particularly contains from about 0.005% to about 95% by weight of the active substance. For example (but not by way of limitation), a dose in a range of from about 10 mg to about 1000 mg once or twice a day could be administered orally.

In another non-limiting embodiment, the composition(s) of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the composition(s) in an aqueous or non-aqueous pharmaceutically acceptable solvent which may also contain suspending agents, sweetening agents, flavoring agents, and preservative agents as are known in the art.

For parenteral administration, for example, the composition(s) may be dissolved in a physiologically acceptable pharmaceutical carrier and administered as either a solution or a suspension. Illustrative of suitable (but non-limiting) pharmaceutical carriers are water, saline, dextrose solutions, fructose solutions, ethanol, or oils of animal, vegetative, or synthetic origin. The pharmaceutical carrier may also contain preservatives and buffers as are known in the art.

When a therapeutically effective amount of the composition(s) is administered by intravenous, cutaneous, or subcutaneous injection, the active agent may be in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the active agent(s), an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition(s) of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the composition(s) selected, the type of wound to be treated, the stage of the wound, and other relevant circumstances using formulation technology known in the art, described, for example, in "*Remington: The Science and Practice of Pharmacy*," incorporated supra.

Additional pharmaceutical methods may be employed to control the duration of action of the composition(s). Increased half-life and/or controlled release preparations may be achieved through the use of polymers to conjugate, complex with, and/or absorb the active substances described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release. The active agent(s) may also be ionically or covalently conjugated to the macromolecules described above, as long as they retain activity.

Another possible method useful in controlling the duration of action of the composition(s) by controlled release preparations and half-life is incorporation of the composition(s) or functional derivatives thereof into particles of a polymeric material such as (but not limited to) polyesters, polyamides, polyamino acids, hydrogels, poly(lactic acid), ethylene vinylacetate copolymers, copolymer micelles of, for example, PEG and poly(l-aspartamide).

EXPERIMENTAL

The embodiments of the present disclosure, having now been generally described, will be more readily understood by reference to the following examples and embodiments, which are included merely for purposes of illustration of certain aspects and embodiments of the present disclosure, and are not intended to be limiting. The following detailed examples of systems and/or methods of use of the present disclosure are to be construed, as noted above, only as illustrative, and not as limitations of the disclosure in any way whatsoever. Those skilled in the art will promptly recognize appropriate variations from the various compositions, procedures, and methods.

Materials and Methods

Murine Hyperglycemic Wound Healing

Experimental animals were treated in accordance with the criteria outlined in the PHS Policy on Humane Care and Use of Laboratory Animals, and the "Guide for the Care and Use of Laboratory Animals" (NIH publication 86-23). The animals were under the care of the Department of Animal Resources in AAALAC accredited facilities located in the College of Pharmacy at the University of Oklahoma Health Sciences Center (Oklahoma City, OK). Mice were allowed to acclimate for 2 weeks prior to experimental manipulations. Hyperglycemia was induced utilizing STZ as described in Lee, E. G., et al. (*Interleukin 6 Function in the Skin and Isolated Keratinocytes Is Modulated by Hyperglycemia*. J Immunol Res, 2019. 2019: p. 5087847). Mice were allowed to remain hyperglycemic (>300 mg/dl) for eight weeks, after which 4 mm full thickness "splinted" punch biopsy wounds were administered as described in Galiano, R. D., et al. (*Quantitative and reproducible murine model of excisional wound healing*. Wound Repair Regen, 2004. 12 (4): p. 485-92). Wounds were treated with 100 µl of anti-mouse CCR3 neutralizing antibody (100 µg/ml, R&D Systems, Minneapolis MN) daily after day 7 post wounding and photographed daily until fully healed. Wound healing and closure was assessed versus a 4 mm circular standard placed in the photographic field by image analysis of wound area.

Human Epidermal Keratinocyte Culture and Wounding Model

Neonatal human epidermal keratinocytes (HEKn, ThermoFisher, Waltham, MA) were cultured according to manufacturer's instructions. HEKn cultures at 70% confluency were wounded by using a 1 mL pipette tip to scrape horizontally and vertically eight times for a 60-mm tissue culture plate, and two times for each well of an 8-well chamber slide. Intact cell cultures served as controls.

Semi-Quantitative PCR

RNA was isolated and cDNA synthesized as described in Gallucci, R. M., et al. (*Interleukin 6 indirectly induces keratinocyte migration*. J Invest Dermatol, 2004. 122 (3): p. 764-72). Quantitative real time (RT)-PCR was performed on Applied Biosystems StepOnePlus (ThermoFisher, Waltham, MA). Gene expression was normalized to 28s using the ΔΔCT method. Primers were custom synthesized by Invitrogen (Waltham, MA) and contained the sequences shown in Table 3.

TABLE 3

| | Primer Sequences (5' > 3' Direction) | |
|---|---|---|
| CCR3: | 5' primer:<br>ATGCTGGTGACAGAGGTCAT<br>(SEQ ID NO: 1) | 3' primer:<br>AGGTGAGTGTGGAAGGCTTA<br>(SEQ ID NO: 2) |
| CCL24: | 5' primer:<br>GGAGTGGGTCCAGAGGTACA<br>(SEQ ID NO: 3) | 3' primer:<br>TTAGCAGGTGGTTTGGTTGC<br>(SEQ ID NO: 4) |
| CCL26: | 5' primer:<br>GCCTGATTTGCAGCATCATGATGG<br>(SEQ ID NO: 5) | 3' primer:<br>CGGATGACAATTCAGCTGAGTCAC<br>(SEQ ID NO: 6) |
| Keratin 1: | 5' primer:<br>TGACCCTGAGATCCAAAAGGTG<br>(SEQ ID NO: 7) | 3' primer:<br>CCGAATCCAACCGAGATTGAT<br>(SEQ ID NO: 8) |
| Keratin 10: | 5' primer:<br>ATGCAGAATCTGAATGACCGCT<br>(SEQ ID NO: 9) | 3' primer:<br>AAGTCATCAGCTGCCAGCCTT<br>(SEQ ID NO: 10) |
| Keratin 16: | 5' primer:<br>ACACATCCGTGGTGCTATCCA<br>(SEQ ID NO: 11) | 3' primer:<br>GGTTGGCACACTGCTTCTTGA<br>(SEQ ID NO: 12) |
| Keratin 17: | 5' primer:<br>GCTCAGCATGAAAGCATCCCT<br>(SEQ ID NO: 13) | 3' primer:<br>TTCCACAATGGTACGCACCTG<br>(SEQ ID NO: 14) |

Immunocytochemistry

HEKn cultures were grown to confluency on collagen I coated 8-well chamber slides. Sixteen hours post-wounding, cells were fixed with 4% paraformaldehyde, and then blocked with goat serum for 1 hour at room temperature. Samples were incubated with either anti-cytokeratin 1 (Abcam, Cambridge, MA), anti-cytokeratin 17 (Abcam, Cambridge, MA), or anti-CCR3 (R&D Systems, Minneapolis, MN) for 1 hour. Anti-cytokeratin 17 staining required an additional permeabilization step. Alexa 488 rat anti-goat IgG monoclonal was used as a secondary antibody (Abcam, Cambridge, MA). Images were obtained using a Leica DM400B microscope, and analyzed with ImageJ (NIH).

Cell Exclusion Zone Assay

HEKn were seeded ($2.0 \times 10^4$ per well) around the barrier of a collagen I coated Oris Cell Migration Assay 96-well plate (Platypus, West Lebanon, NH). Cells were incubated overnight to allow for cell attachment. After incubation, the circular barriers were removed (except for reference wells), and the cells were treated with either anti-CCR3 (R&D Systems, Minneapolis, MN) (2 ug/mL), IgG control (R&D Systems, Minneapolis, MN; 2 μg/mL), CCL24 (Biolegend, San Jose, CA), CCL26 (Biolegend, San Jose, CA), or IGF (ThermoFisher, Waltham, MA; 10 ng/mL) for 16 hours. At the end of the experiment, Calcein-AM (Life Technologies, Carlsbad, CA) (2 μM) was added prior to obtaining images with a Nikon TE2000-E inverted epi-fluorescence microscope (2× objective). ImageJ (NIH) was utilized to analyze the images.

Proliferation Assay

Cells were plated on a collagen I coated 96-well plate (Corning, New York, NY) at a density of $4 \times 10^3$ cells per well, and then allowed to attach overnight. The next day, cells were treated with CCL24 (Biolegend, San Diego, CA), CCL26 (Biolegend, San Diego, CA), or IGF (ThermoFisher, Waltham, MA) for 16 hours. To assess viability, PrestoBlue (Life Technologies, Carlsbad, CA) was added according to manufacturer's protocol, and results were obtained on a microplate reader (BioTek, Winooski, VT).

Cell Cycle Analysis

HEKn cultures were grown to confluency and then treated with anti-CCR3 (R&D Systems, Minneapolis, MN; 2 μg/mL), CCL24 (Biolegend, San Diego, CA; 50 ng/mL), or CCL26 (Biolegend, San Diego, CA; 50 ng/mL). Single cell suspensions were obtained and stained with FxCycle PI/RNase (ThermoFisher, Waltham, MA) according to manufacturer's instructions. Data was obtained using a S1000EXi flow cytometer (Stratedigm, San Jose, CA) and analyzed with FlowJo software (TreeStar, Ashland, OR).

Statistical Analysis

All experiments were replicated, and data was expressed as mean±SD. Statistical significance was determined using a two-tailed unpaired Student's t test or one-way analysis of variance with Dunnett's post-hoc test. A p value of <0.05 was considered statistically significant.

Results

Keratinocyte CCR3 Expression Following In Vitro Wounding

Figure 1B:
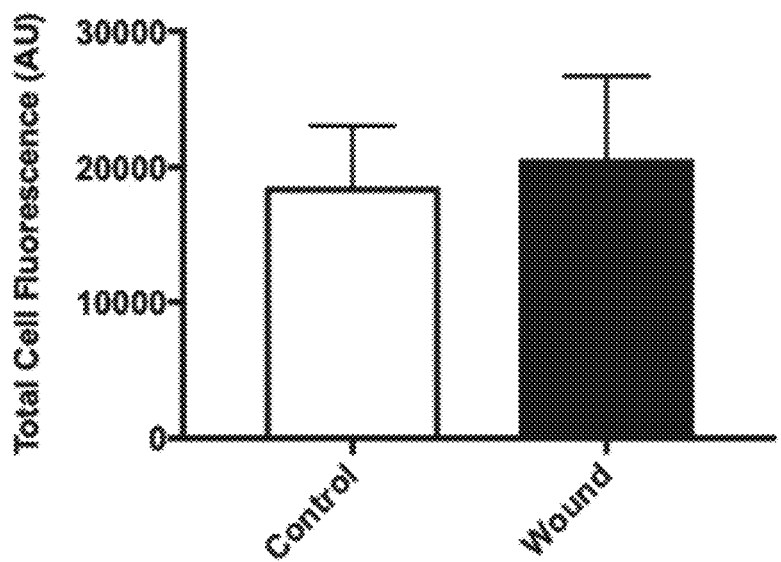
FIG. 1B shows that, for determination of CCR3 protein expression, keratinocytes of FIG. 1A were grown in 8-well chamber slides, and immunocytochemistry was completed 16 hours post-wounding. Bar graph is expressed as mean±SD, $*p<0.05$ versus control (intact cells).
Figure 1C:
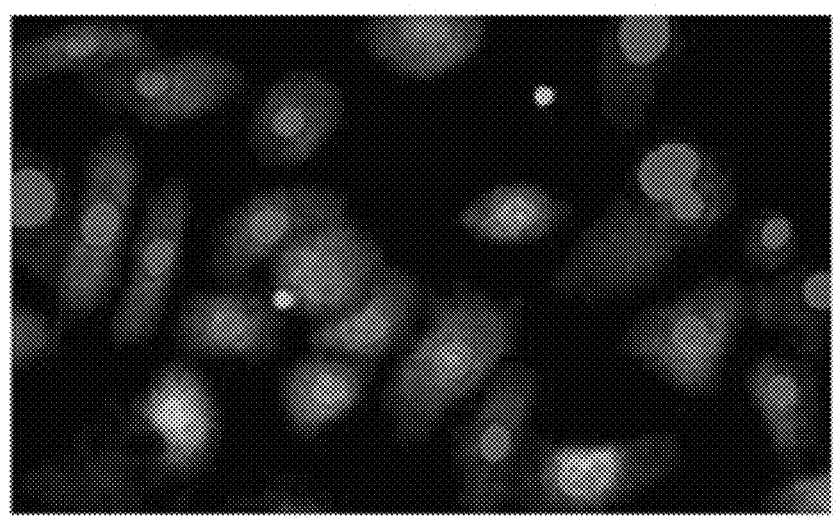
FIG. 1C shows representative photomicrographs of keratinocytes of FIG. 1B.
Figure 1C:
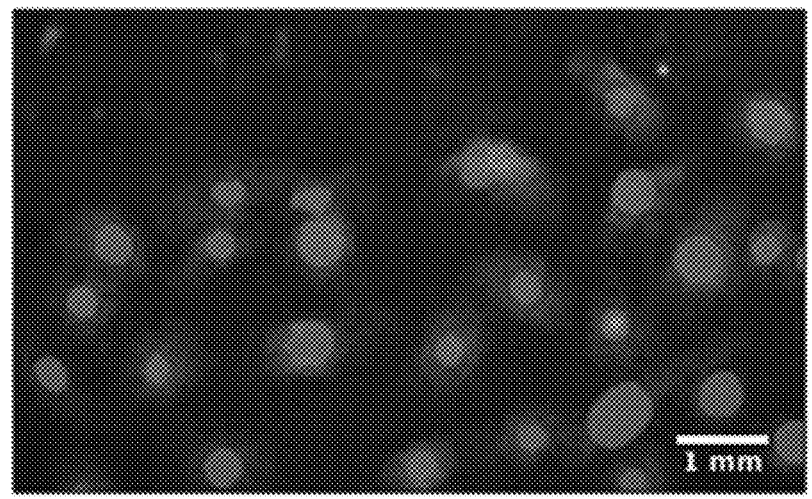

Although keratinocytes express CCR3, it has been unknown if keratinocyte CCR3 expression is modulated during the wound repair process. To determine whether or not wounding/cellular damage affects keratinocyte CCR3 expression, neonatal human epidermal keratinocytes (HEKn) were cultured on type I collagen to confluency and then subjected to a scratch wound assay. Total RNA was isolated from keratinocytes at 30 minutes, 1 hour, and 2 hours post-wounding, and CCR3 gene expression was assessed by quantitative PCR. As seen in FIG. 1A, CCR3 mRNA expression significantly increased 2 hours post-wounding. To determine if the observed increase in mRNA corresponded with protein, immunocytochemistry revealed that CCR3 expression did not significantly differ between wounded keratinocytes and control (FIGS. 1B-1C).

CCR3 Inhibition Promotes Keratinocyte In Vitro Wound Healing

Figure 2A:
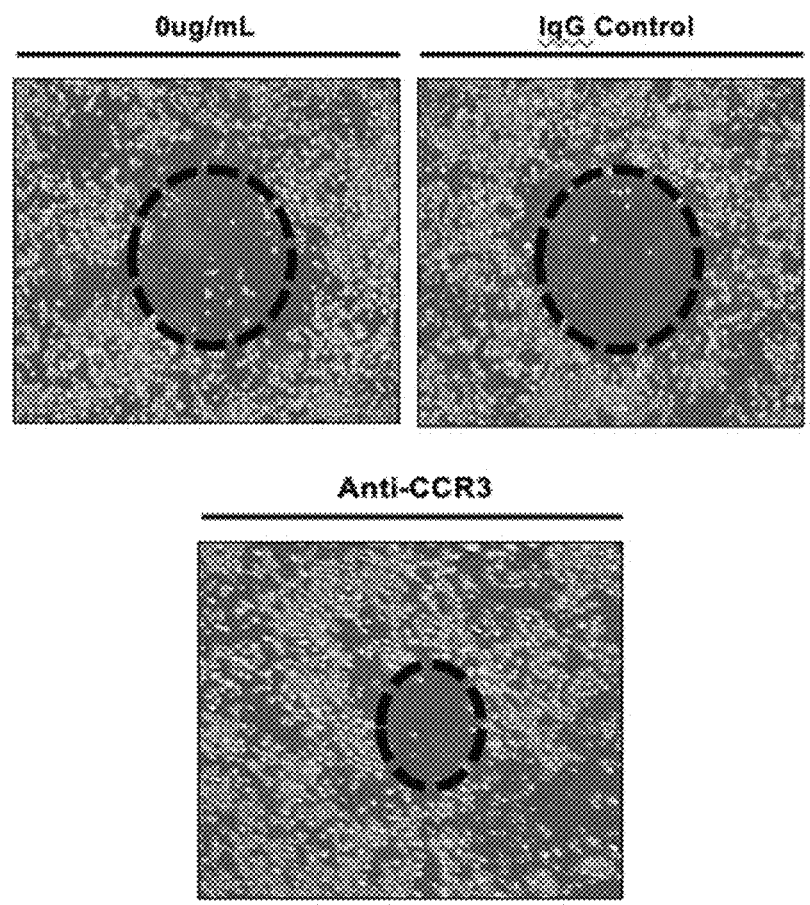
FIG. 2A shows representative images of HEKn cell cultures which received no treatment (0 µg/mL) or were treated with IgG control (2 µg/mL) or anti-CCR3 (2 µg/mL) for 16 hours. Cells were labeled with calcein-AM, and cell migration was measured from images with utilization of ImageJ (National Institutes of Health, Bethesda, MD). Results indicate that CCR3 inhibition promotes in vitro wound healing in keratinocytes.
Figure 2B:
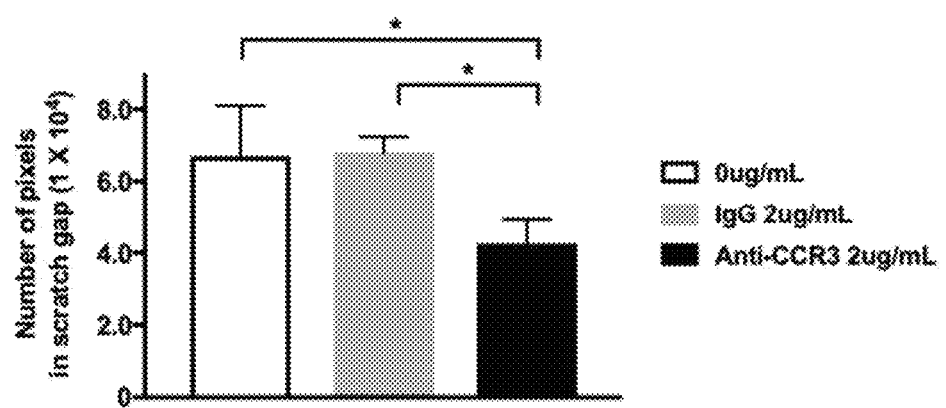
FIG. 2B shows a bar graph in which the results of FIG. 2A are quantified. Bars are expressed as mean±SD, $*p<0.05$ versus control (0 ug/mL and IgG).

During the wound repair process, keratinocytes restore the injured epidermis by re-epithelialization, which involves keratinocyte proliferation, migration, and differentiation. To determine whether keratinocyte CCR3 function could be involved in epithelialization, keratinocyte wound closure was assessed following treatment with CCR3 neutralizing antibody (anti-CCR3). Indeed, HEKn wound closure was significantly increased following treatment with 2 μg/mL of anti-CCR3 compared to control, as determined by a cell exclusion zone assay (FIGS. 2A-2B).

Figure 3A:
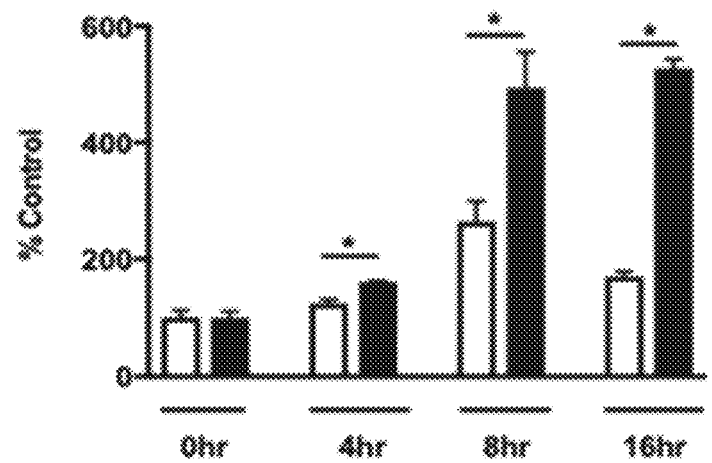
FIG. 3A shows that CCR3 inhibition modulates expression of keratin 1. HEKn cultures were grown to confluency and wounded. Total cellular RNA was prepared, and expression of keratin 1 mRNA was determined by real-time polymerase chain reaction. Open bars are control. Solid bars are anti-CCR3 treatment. Bars are expressed as mean±SD, $*p<0.05$ versus control (0 hr).
Figure 3B:
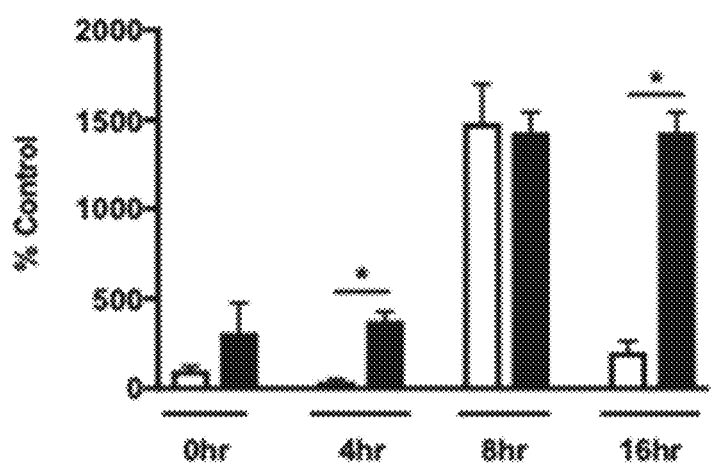
FIG. 3B shows that CCR3 inhibition modulates expression of keratin 10. HEKn cultures were grown to confluency and wounded. Total cellular RNA was prepared, and expression of keratin 10 mRNA was determined by real-time polymerase chain reaction. Open bars are control. Solid bars are anti-CCR3 treatment. Bars are expressed as mean±SD, $*p<0.05$ versus control (0 hr).
Figure 3C:
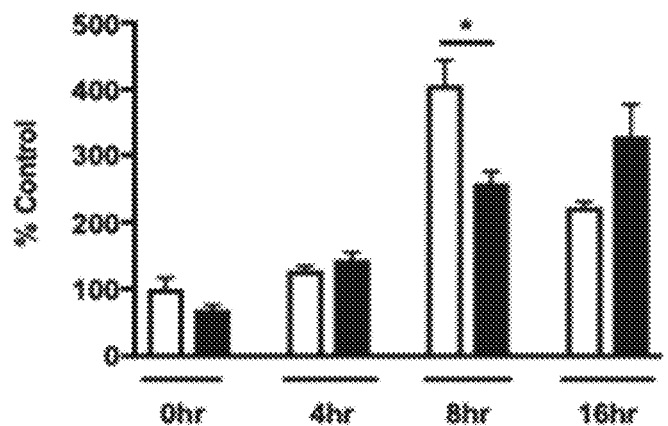
FIG. 3C shows that CCR3 inhibition modulates expression of keratin 16. HEKn cultures were grown to confluency and wounded. Total cellular RNA was prepared, and expression of keratin 16 mRNA was determined by real-time polymerase chain reaction. Open bars are control. Solid bars are anti-CCR3 treatment. Bars are expressed as mean±SD, $*p<0.05$ versus control (0 hr).
Figure 3D:
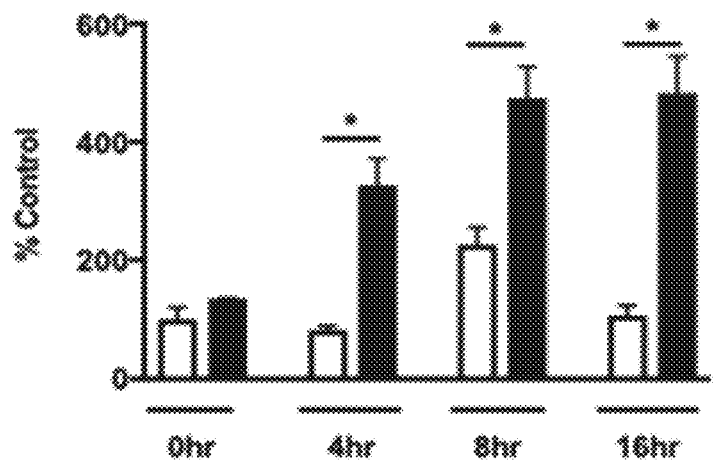
FIG. 3D shows that CCR3 inhibition modulates expression of keratin 17. HEKn cultures were grown to confluency and wounded. Total cellular RNA was prepared, and expression of keratin 17 mRNA was determined by real-time polymerase chain reaction. Open bars are control. Solid bars are anti-CCR3 treatment. Bars are expressed as mean±SD, $*p<0.05$ versus control (0 hr).
Figure 3E:
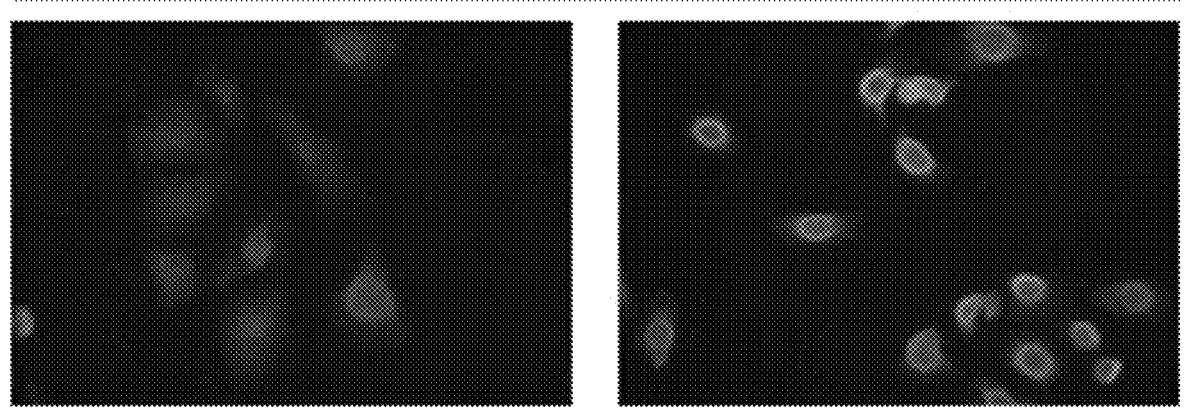
FIG. 3E shows that expression of keratin 1 protein corresponds to keratin 1 mRNA expression (FIG. 3A). Keratinocytes were grown in 8-well chamber slides, and immunocytochemistry was completed 16 hours post-wounding. Bars are expressed as mean±SD, $*p<0.05$ versus intact cells.
Figure 3E:
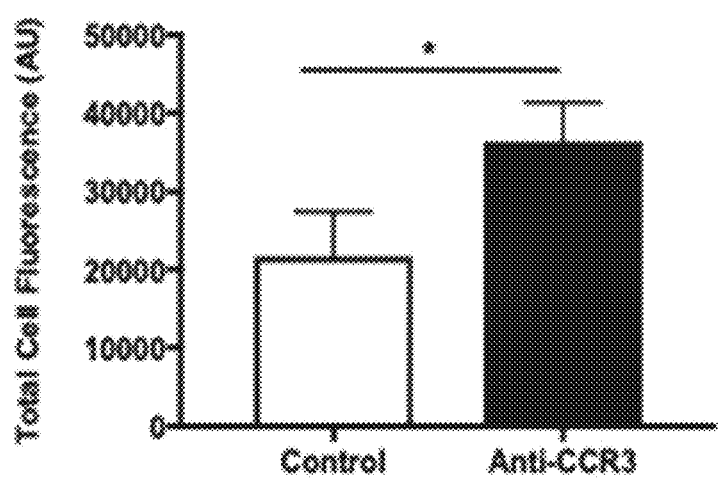
Figure 3F:
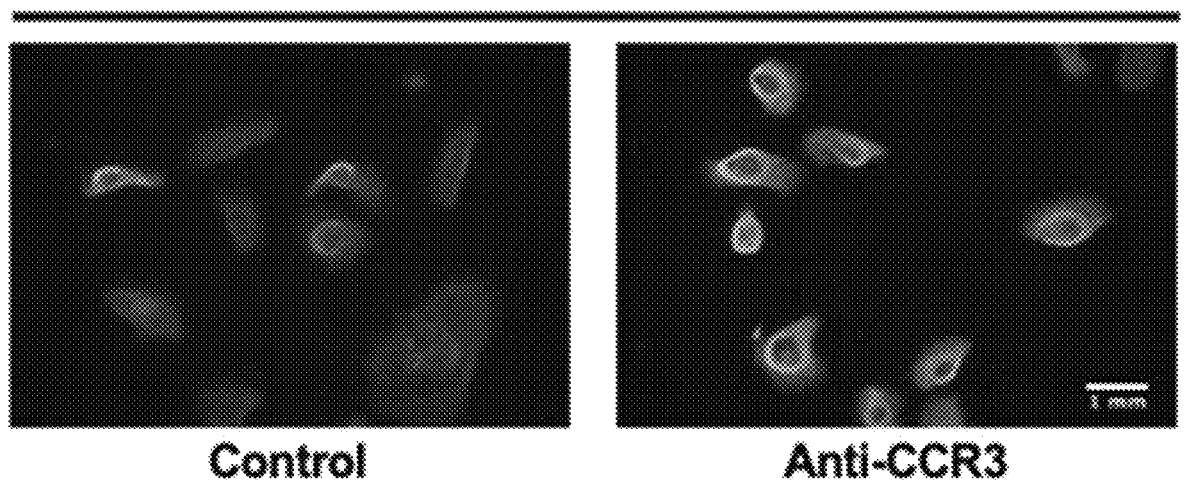
FIG. 3F shows that expression of keratin 17 protein corresponds to keratin 17A mRNA expression (FIG. 3D). Keratinocytes were grown in 8-well chamber slides, and immunocytochemistry was completed 16 hours post-wounding. Bars are expressed as mean±SD, $*p<0.05$ versus intact cells.
Figure 3F:
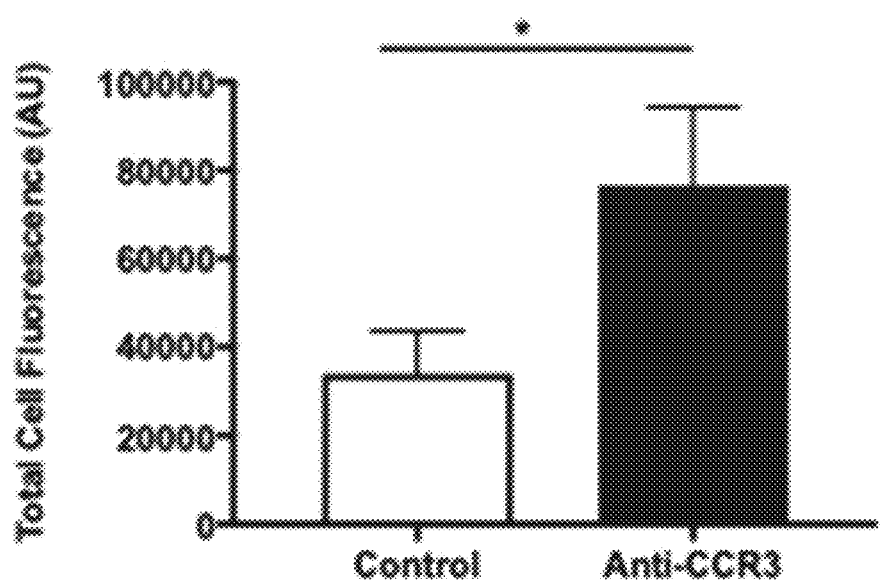

Keratinocyte proliferation, migration, and differentiation are distinguished by differential expression of keratin (K) intermediate filaments. In order to determine if anti-CCR3 treatment alters keratinocyte keratin expression, HEKn cultures were treated with either 0 ng/mL or 2 μg/mL of anti-CCR3 following wounding. Total RNA was isolated at 0 hours, 4 hours, 8 hours, and 16 hours post-wounding, and then K1, K10, K16, and K17 mRNA expression was measured. Anti-CCR3 treated keratinocytes exhibited significantly up-regulated mRNA expression of K1, K10, and K17 at four hours post-wounding, K1 and K17 at eight hours post-wounding, and K1, K10, and K17 at 16 hours post-wounding (FIGS. 3A-3D). As K1 and K17 mRNA expression was up-regulated at each post-wounding time point in anti-CCR3 treated keratinocytes, K1 and K17 protein expression was evaluated to determine if protein resembled mRNA. Indeed, immunocytochemistry revealed significantly increased K1 and K17 keratin expression at 16 hours post-wounding in anti-CCR3 treated HEKn as compared to control (FIGS. 3E-3F).

Effects of CCL24 and CCL26 on Keratinocyte Proliferation and Migration

Figure 4A:
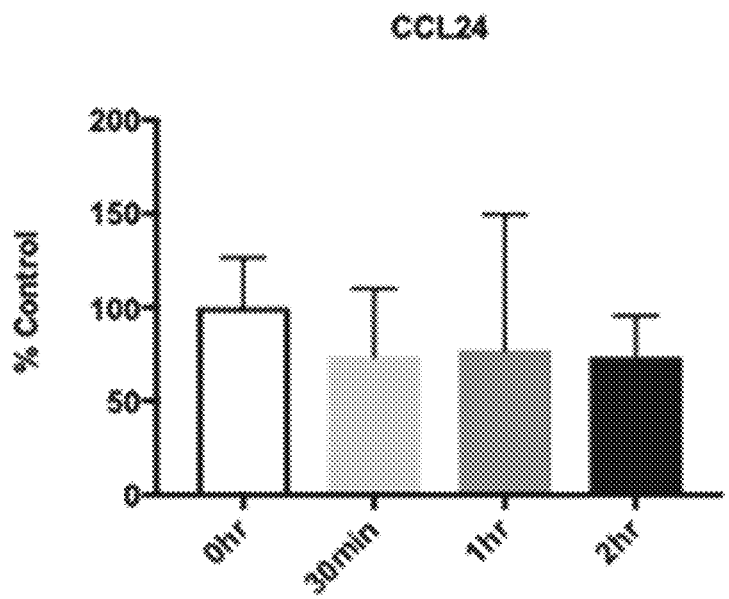
FIG. 4A shows production of Chemokine (C-C motif) ligand 24 (CCL24) in keratinocytes after wounding. Cells (HEKn) were grown to confluency and wounded. Total cellular RNA was prepared, and expression of CCL24 mRNA over 0-2 hours was determined by real-time polymerase chain reaction. Bars are expressed as mean±SD, $*p<0.05$ versus control (0 hr).
Figure 4B:
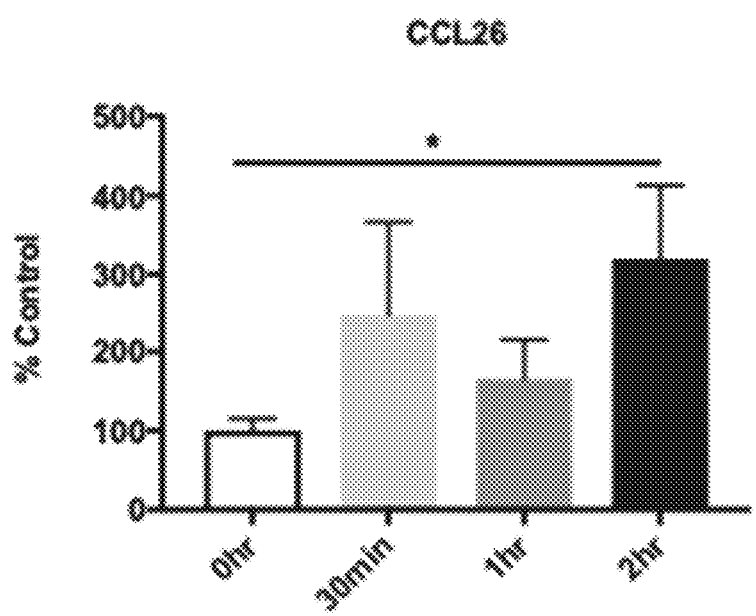
FIG. 4B shows production of Chemokine (C-C motif) ligand 26 (CCL26) in keratinocytes after wounding. Cells (HEKn) were grown to confluency and wounded. Total cellular RNA was prepared, and expression of CCL26 mRNA over 0-2 hours was determined by real-time polymerase chain reaction. Bars are expressed as mean±SD, *p<0.05 versus control (0 hr).
Figure 4C:
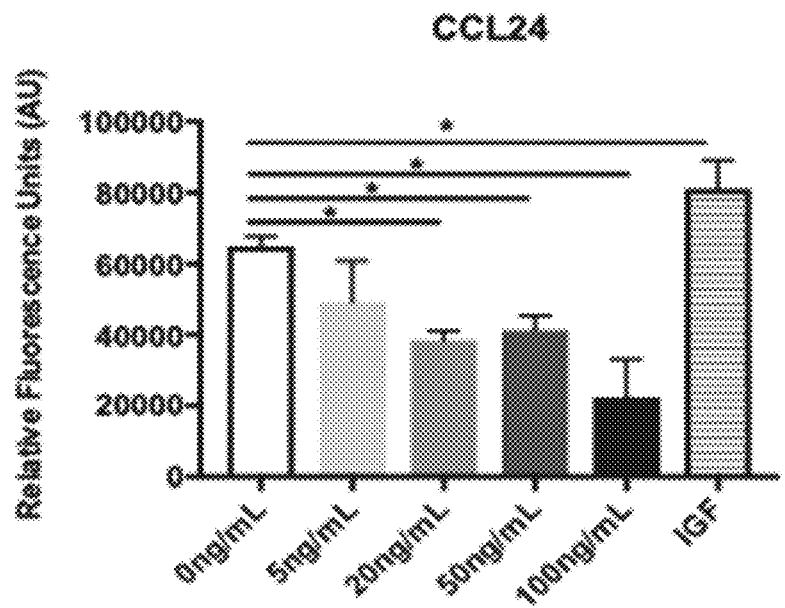
FIG. 4C shows the effect of CCL24 on keratinocyte proliferation. Cells (HEKn) were grown to confluency and wounded. Keratinocytes were treated with CCL24 for 16 hours. Cells were subjected to PrestoBlue for determination of proliferation from images using ImageJ. Bars are expressed as mean±SD, *p<0.05 versus untreated control.
Figure 4D:
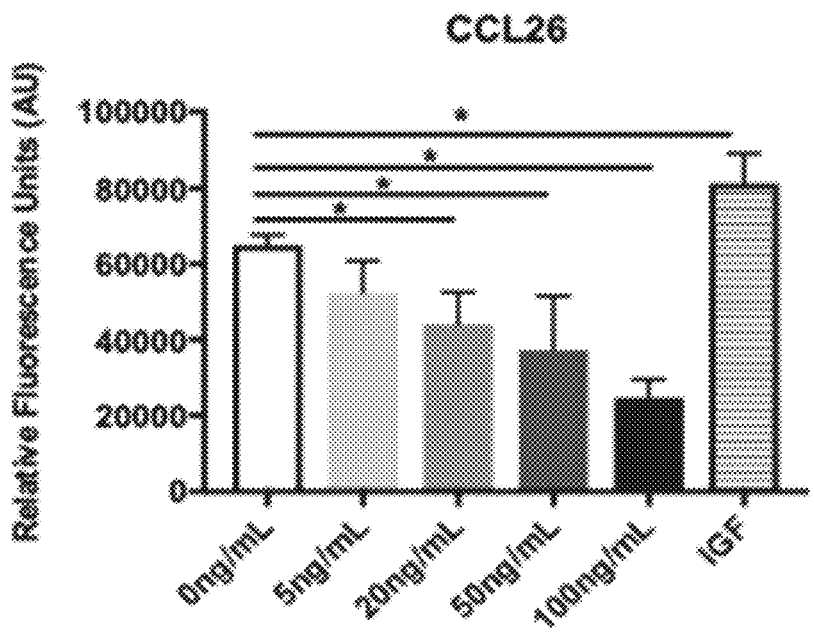
FIG. 4D shows the effect of CCL26 on keratinocyte proliferation. Cells (HEKn) were grown to confluency and wounded. Keratinocytes were treated with CCL26 for 16 hours. Cells were subjected to PrestoBlue for determination of proliferation from images using ImageJ. Bars are expressed as mean±SD, *p<0.05 versus untreated control.
Figure 4E:
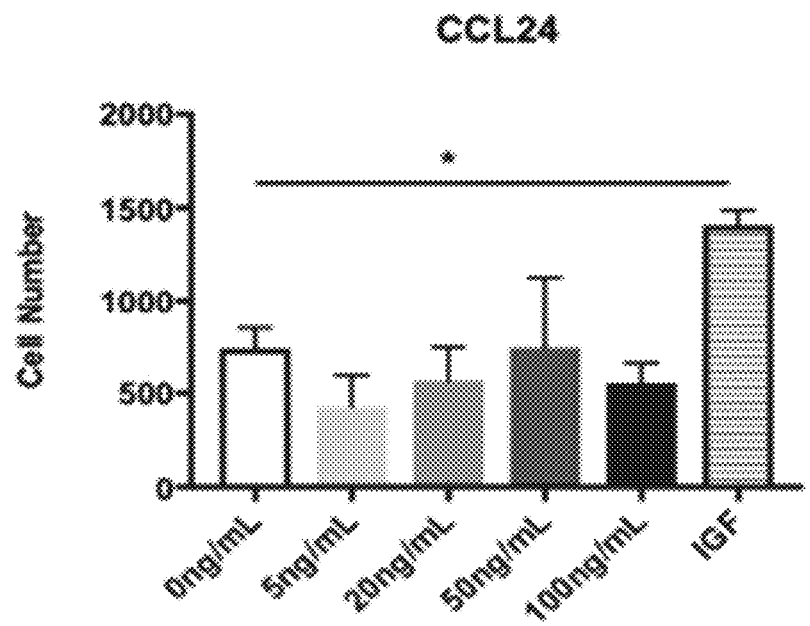
FIG. 4E shows the effect of CCL24 on keratinocyte migration. Cells (HEKn) were grown to confluency and wounded. Keratinocytes were treated with CCL24 for 16 hours. Cells were labeled with calcein-AM to determine cell migration from images using ImageJ. Bars are expressed as mean±SD, *p<0.05 versus untreated control.
Figure 4F:
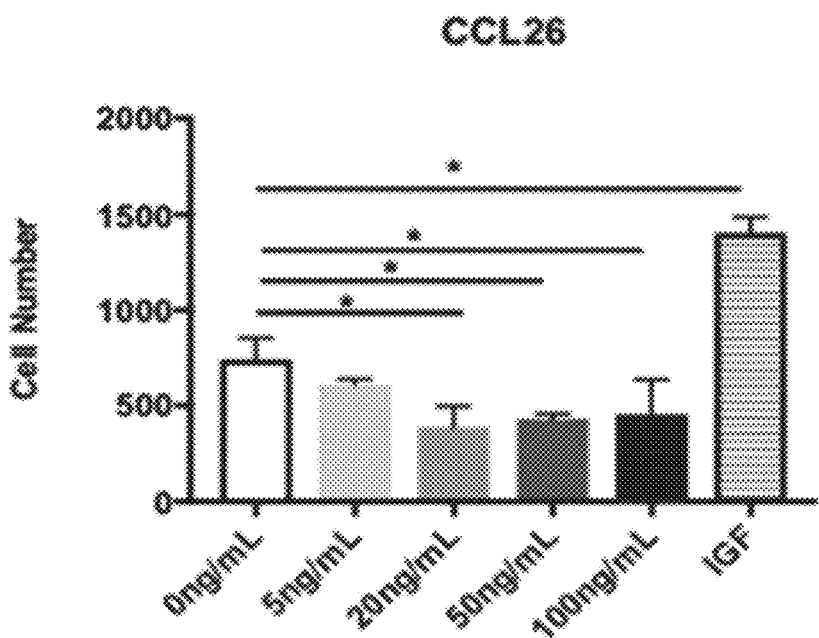
FIG. 4F shows the effect of CCL26 on keratinocyte migration. Cells (HEKn) were grown to confluency and wounded. Keratinocytes were treated with CCL26 for 16 hours. Cells were labeled with calcein-AM to determine cell migration from images using ImageJ. Bars are expressed as mean±SD, *p<0.05 versus untreated control.

As inhibition of CCR3 was shown to promote in vitro wound healing, keratinocyte expression of the CCR3-specific ligands, CCL24 (eotaxin-2) and CCL26 (eotaxin-3), was evaluated following wounding. Total RNA was isolated from keratinocytes at 0 hours, 30 minutes, 1 hour, and 2 hours post-wounding, and quantitative PCR was used to measure CCL24 and CCL26 mRNA expression. Expression of CCL26 was significantly up-regulated in keratinocytes at 2 hours post-wounding (FIG. 4B); however, CCL24 did not differ significantly between wounded keratinocytes and control (FIG. 4A). As chemokines are essential mediators of wound healing, the effect of CCL24 and CCL26 on keratinocyte proliferation and migration was evaluated. Treatment with CCL24 at concentrations of 20 ng/mL, 50 ng/mL, and 100 ng/mL significantly reduced keratinocyte proliferation (FIG. 4C), as well as, CCL26 at 20 ng/mL, 50 ng/mL and 100 ng/mL (FIG. 4D). However, treatment with CCL24 and CCL26 did not significantly alter keratinocyte migration (FIGS. 4E-4F).

CCR3 antagonism promotes closure of wounds from hyperglycemic mice

Figure 5:
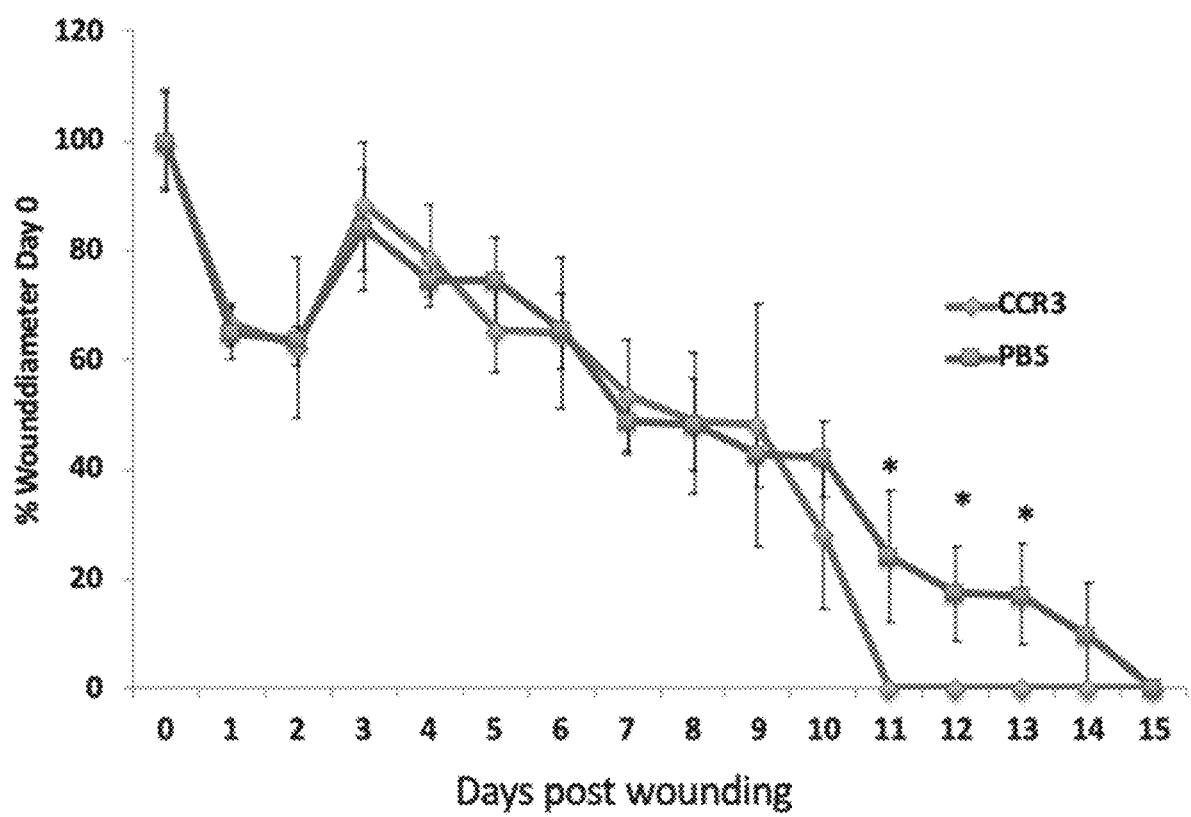
FIG. 5 shows that CCR3 blockade promotes faster healing in diabetic mice. STZ treated hyperglycemic mice were subjected to a 4 mm full thickness punch biopsy splinted wound. Wounds were treated with 100 μl of 100 μg/ml anti-CCR3 antibody or PBS control daily starting day 5 post wounding. Digital photographs of wounds were taken and standardized to a 4 mm paper disk in frame and analyzed via ImageJ. Data are % initial wound diameter, +/−SE, *significantly different from PBS treated, n=10, p<0.05 via 1 factor ANOVA.
Figure 6:
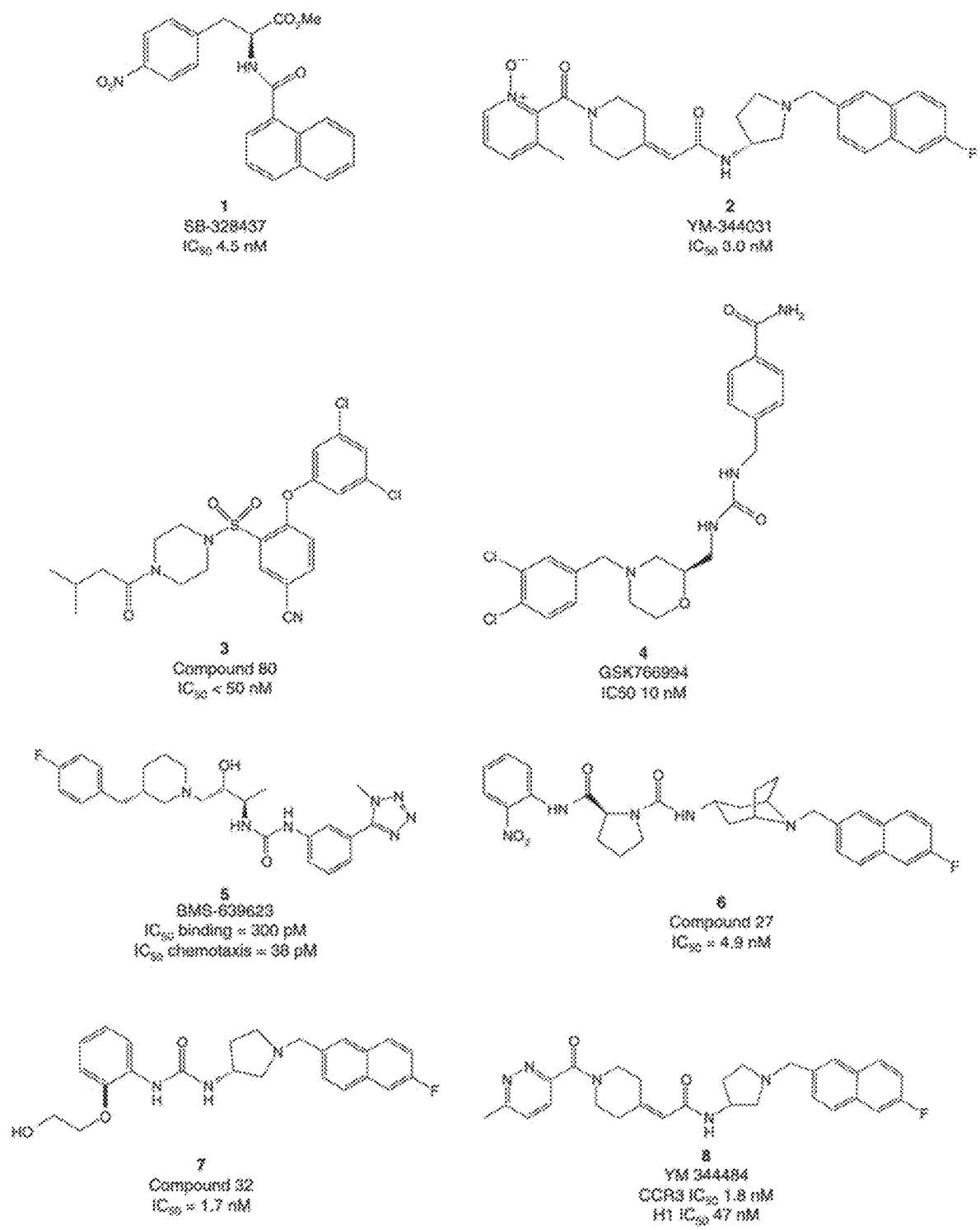
FIG. 6 shows examples of small molecule CCR3 antagonists that can be used in non-limiting embodiments of the present disclosure.
Figure 7:
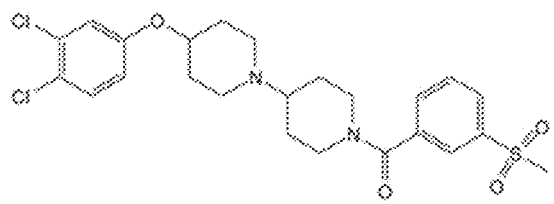
FIG. 7 shows examples of other small molecule CCR3 antagonists that can be used in non-limiting embodiments of the present disclosure.
Figure 7:
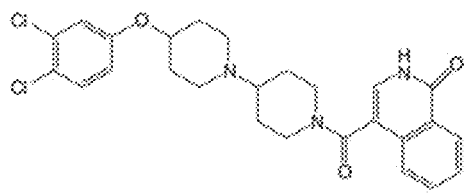
Figure 7:
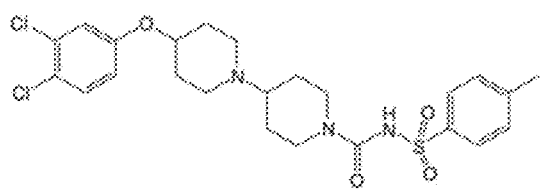
Figure 7:
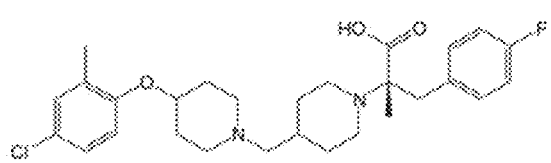
Figure 7:
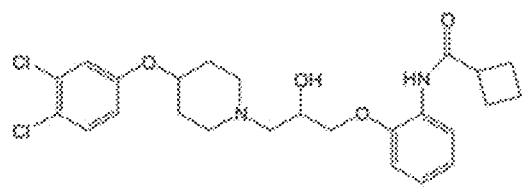
Figure 7:
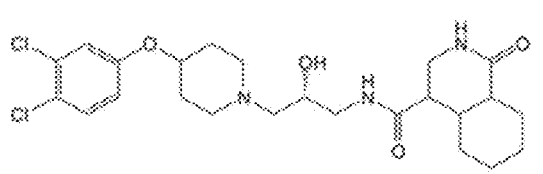
Figure 7:
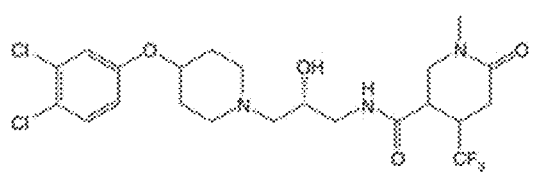
Figure 8:
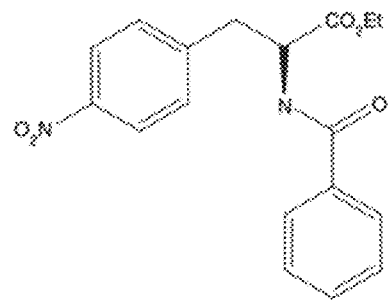
FIG. 8 shows examples of other small molecule CCR3 antagonists that can be used in non-limiting embodiments of the present disclosure.
Figure 8:
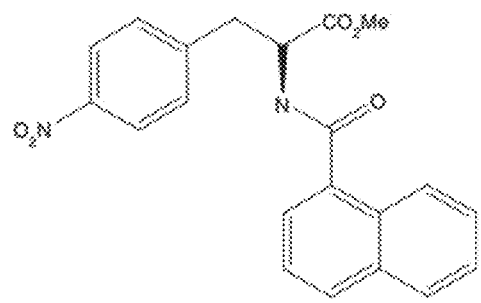
Figure 8:
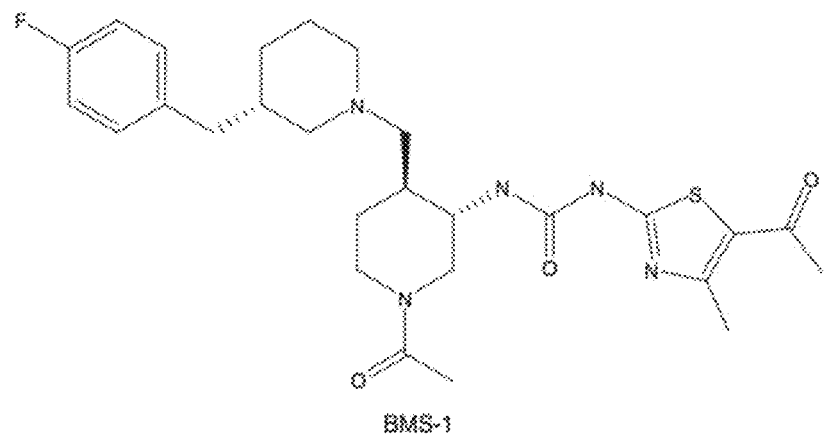
Figure 8:
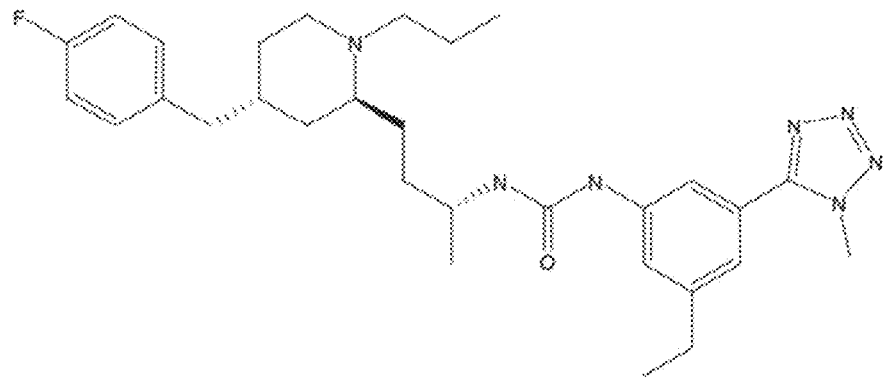
Figure 9:
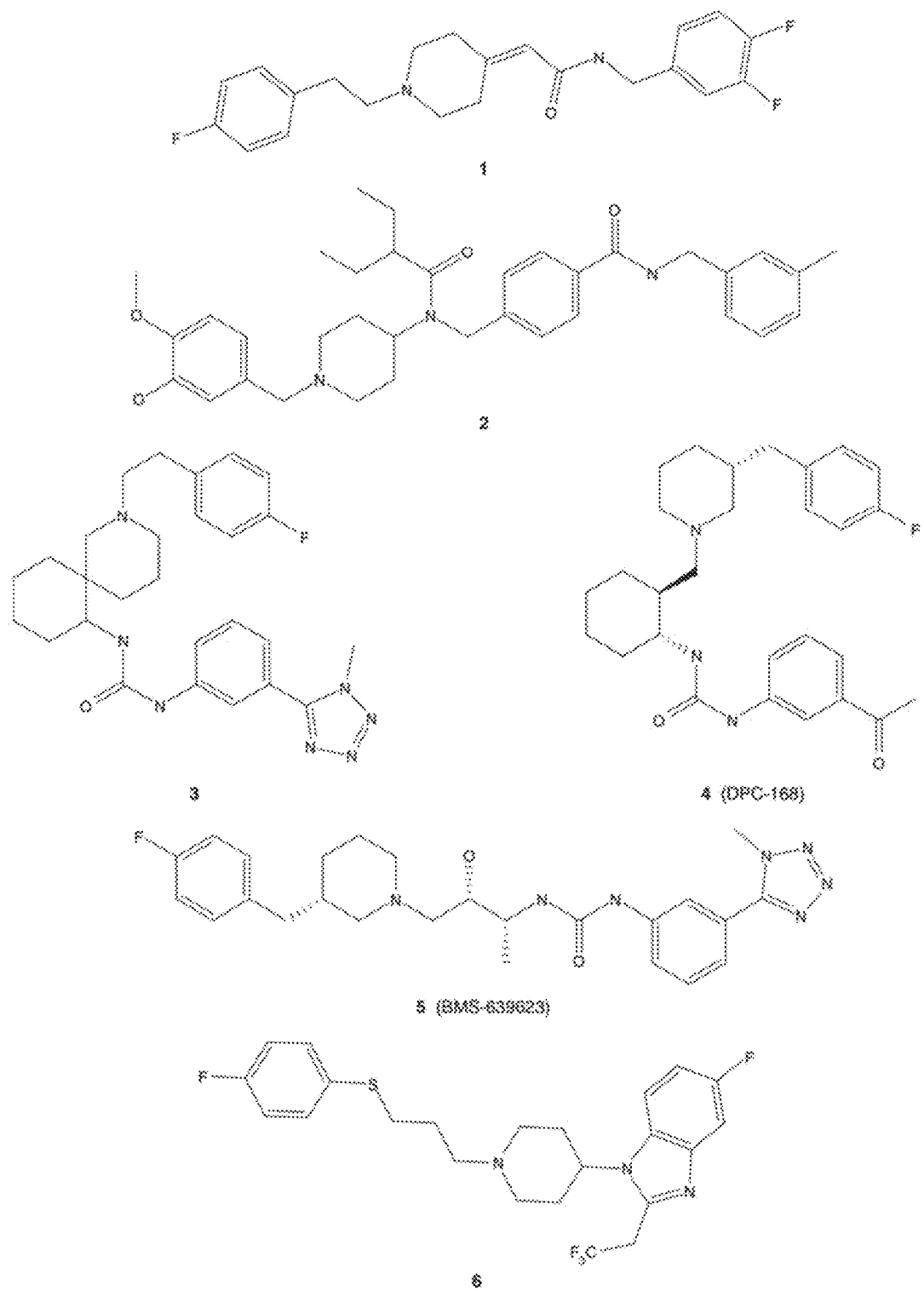
FIG. 9 shows examples of other small molecule CCR3 antagonists that can be used in non-limiting embodiments of the present disclosure.
Figure 10:
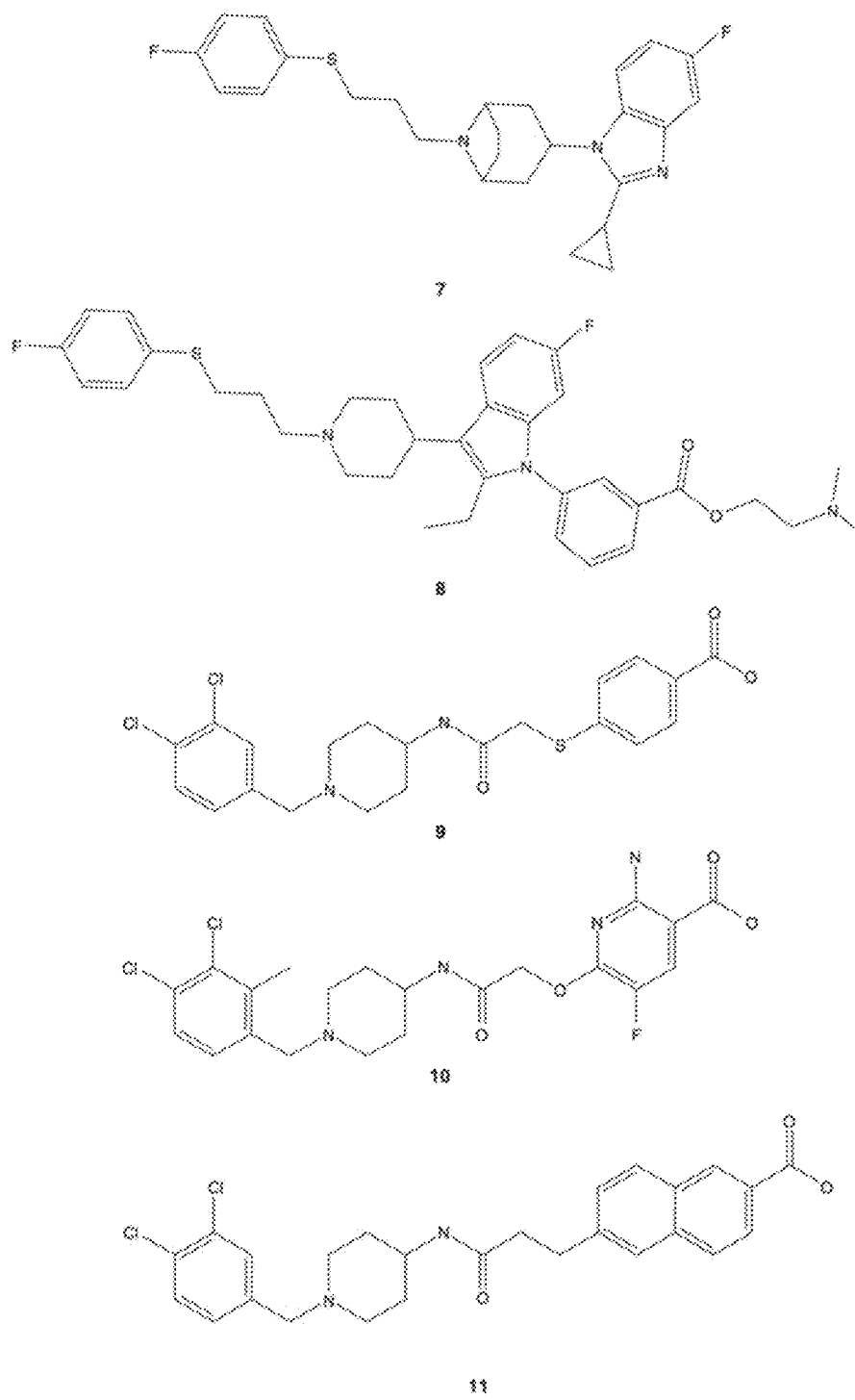
FIG. 10 shows examples of other small molecule CCR3 antagonists that can be used in non-limiting embodiments of the present disclosure.
Figure 11:
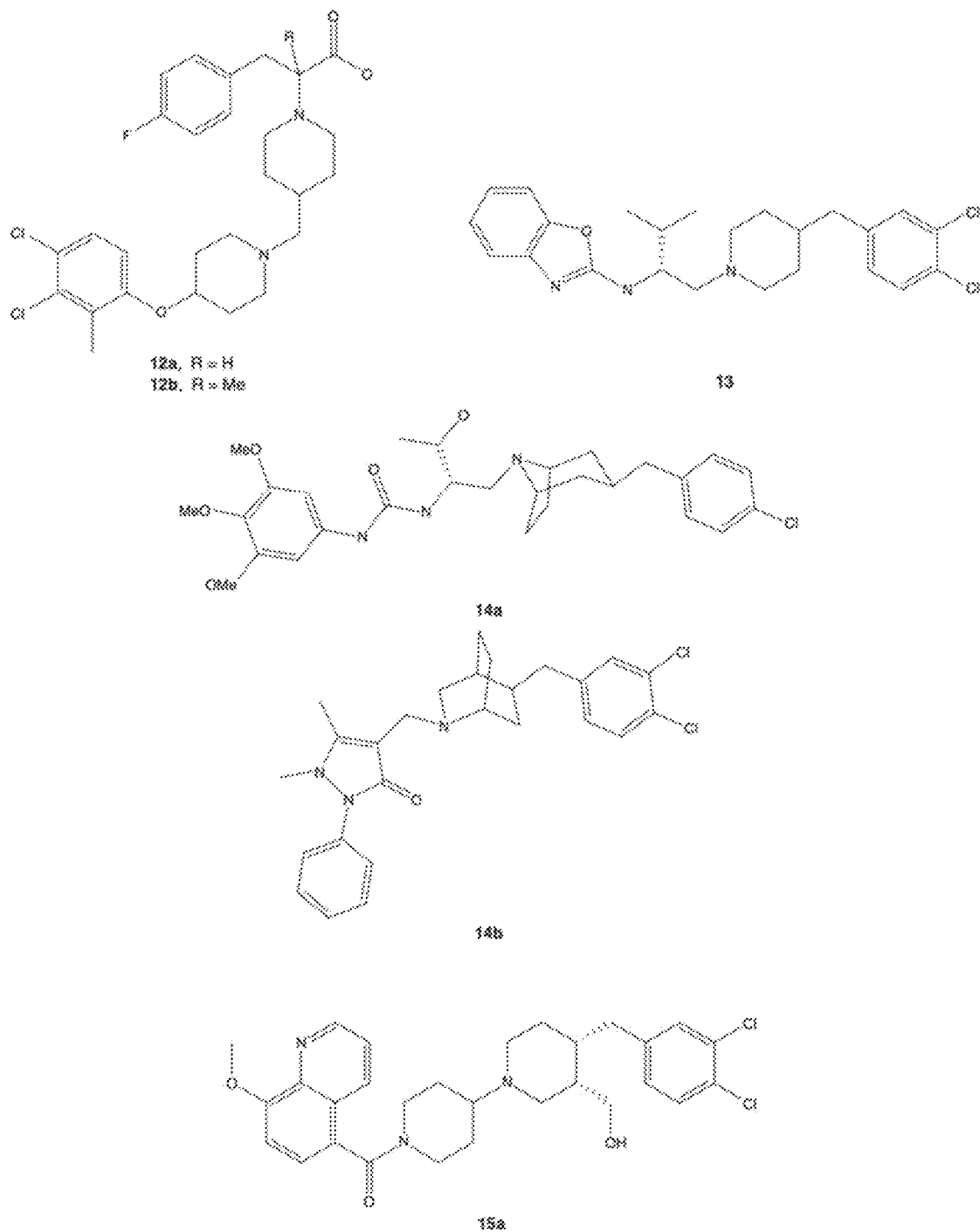
FIG. 11 shows examples of other small molecule CCR3 antagonists that can be used in non-limiting embodiments of the present disclosure.
Figure 12:
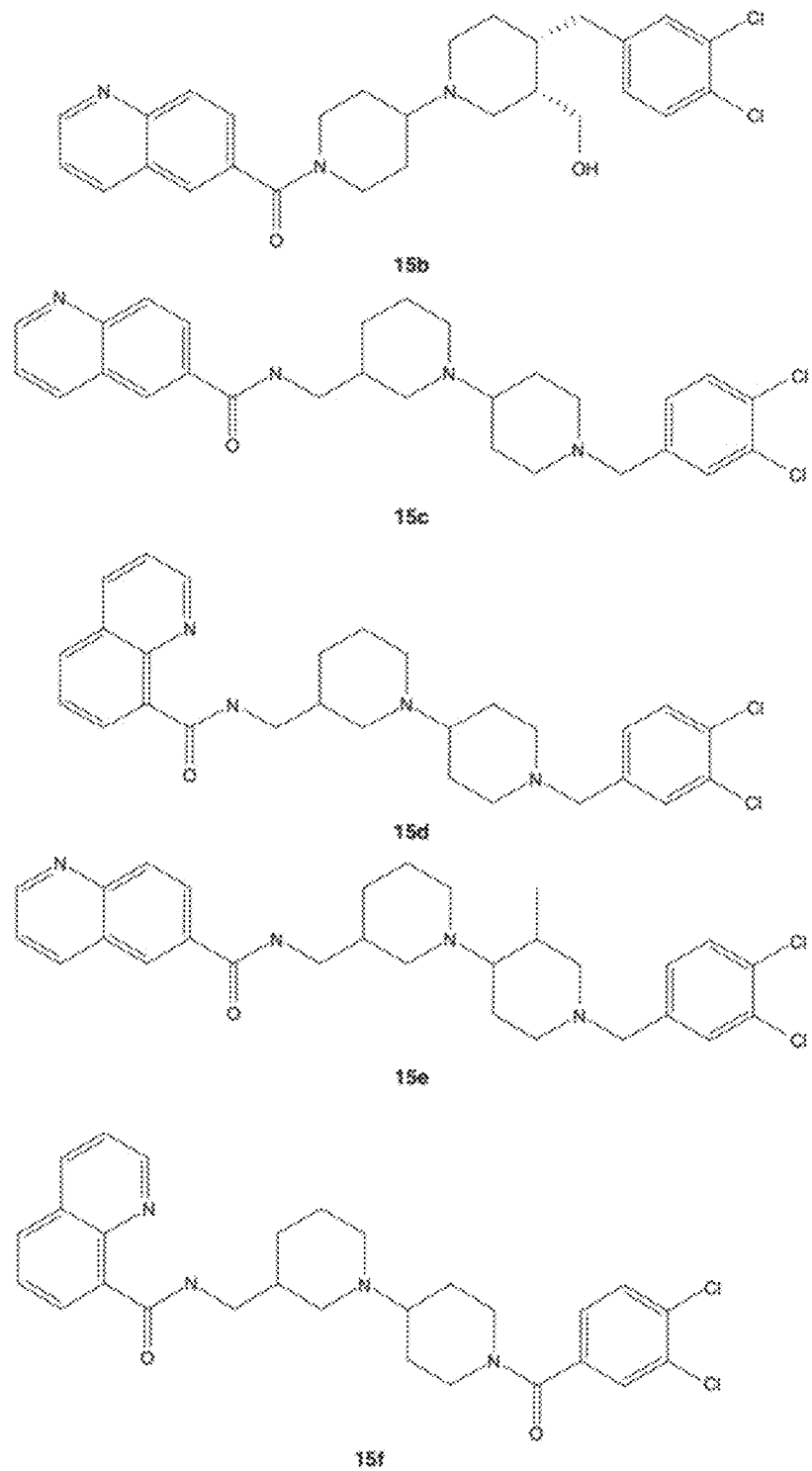
FIG. 12 shows examples of other small molecule CCR3 antagonists that can be used in non-limiting embodiments of the present disclosure.
Figure 13:
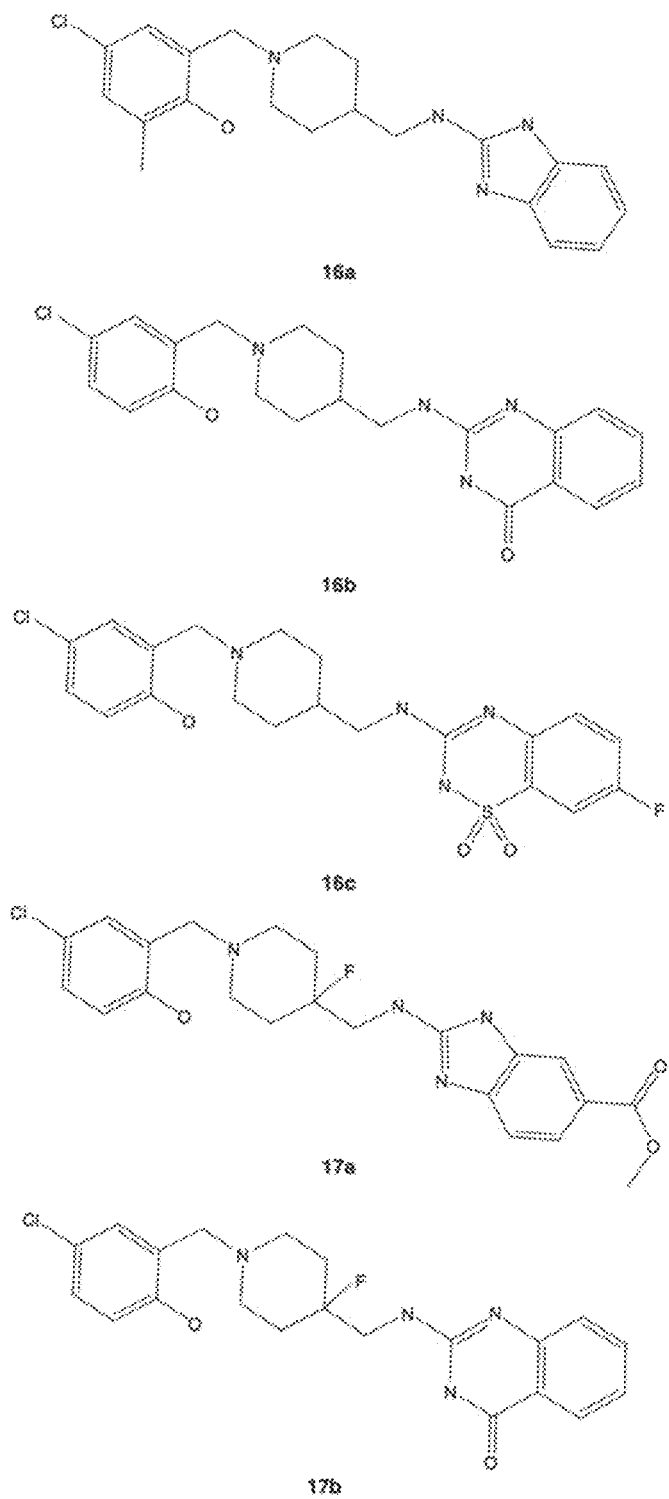
FIG. 13 shows examples of other small molecule CCR3 antagonists that can be used in non-limiting embodiments of the present disclosure.
Figure 14:
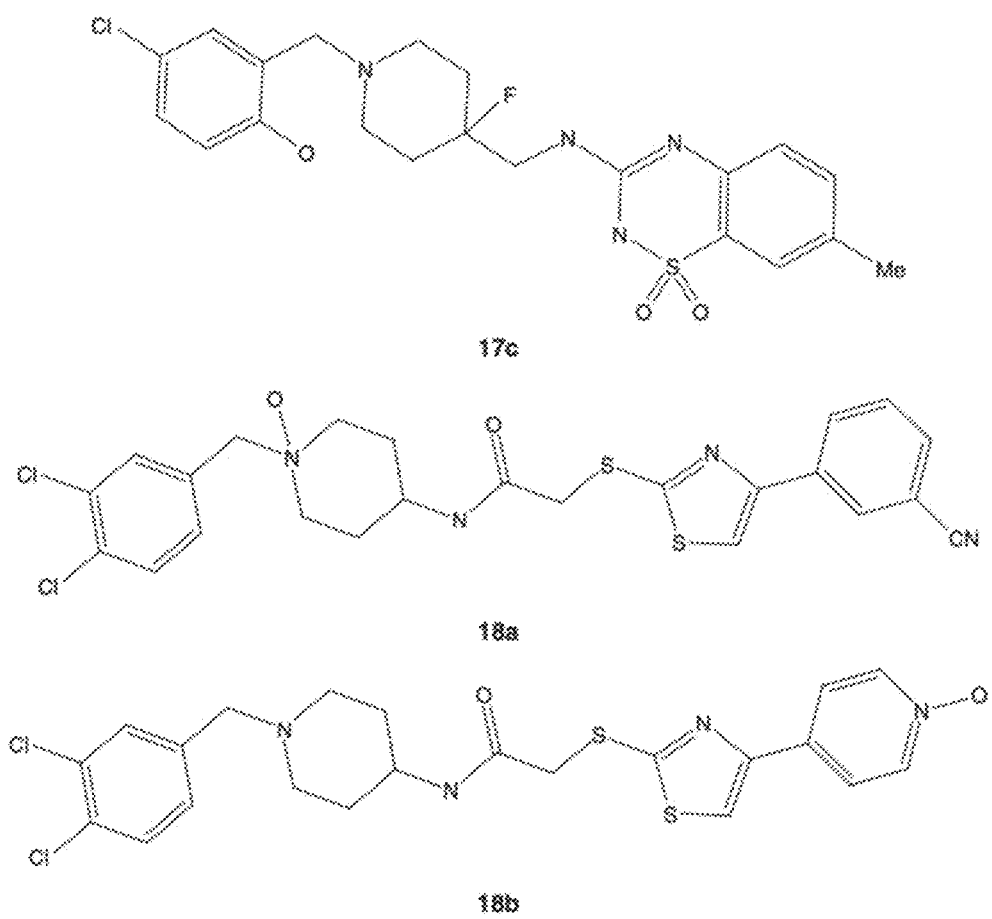
FIG. 14 shows examples of other small molecule CCR3 antagonists that can be used in non-limiting embodiments of the present disclosure.
Figure 15:
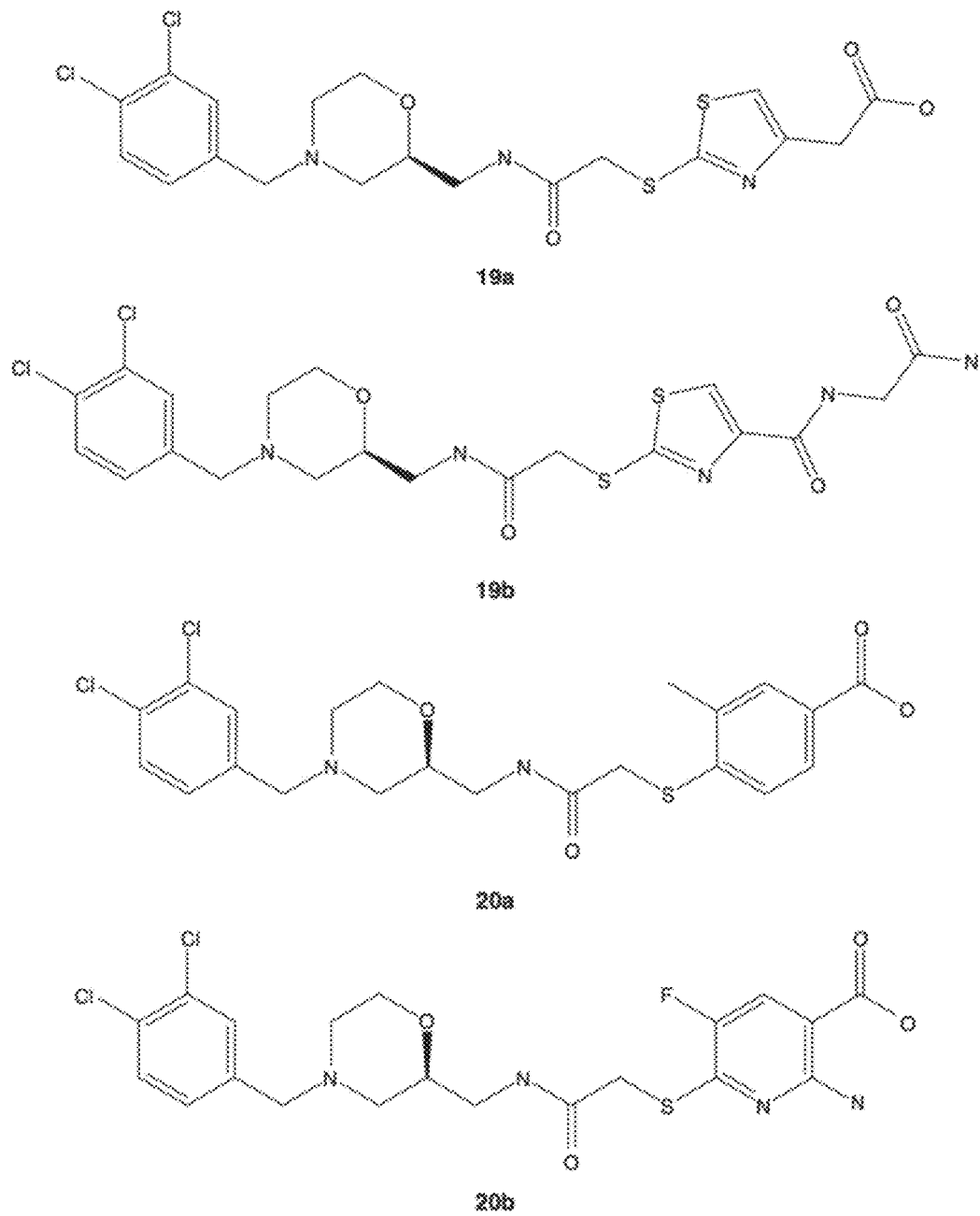
FIG. 15 shows examples of other small molecule CCR3 antagonists that can be used in non-limiting embodiments of the present disclosure.
Figure 16:
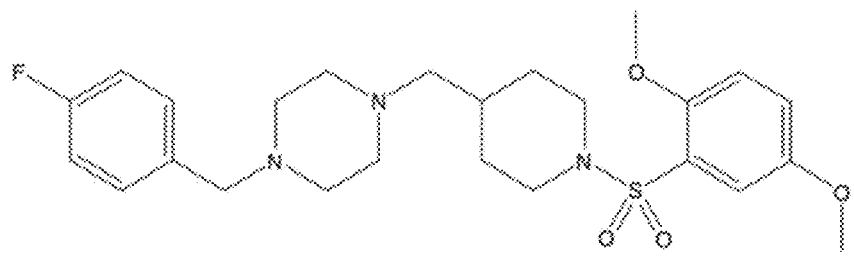
FIG. 16 shows examples of other small molecule CCR3 antagonists that can be used in non-limiting embodiments of the present disclosure.
Figure 16:
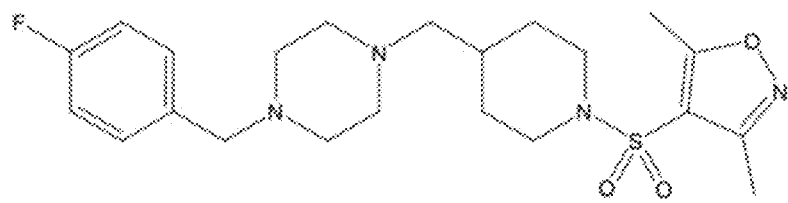
Figure 16:
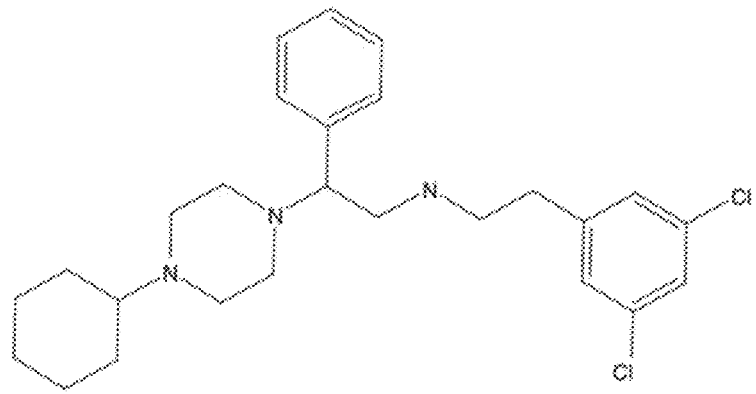
Figure 17:
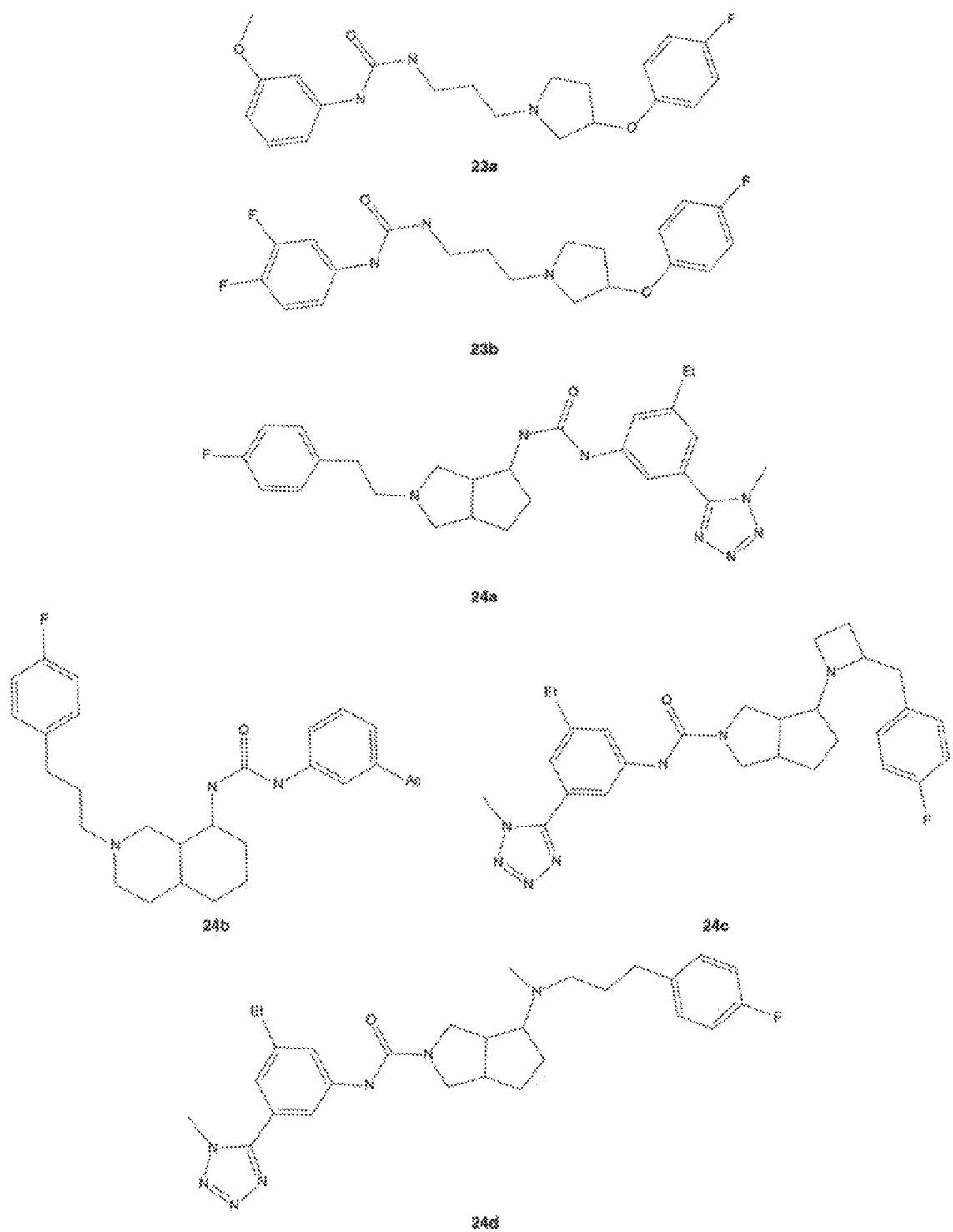
FIG. 17 shows examples of other small molecule CCR3 antagonists that can be used in non-limiting embodiments of the present disclosure.
Figure 18:
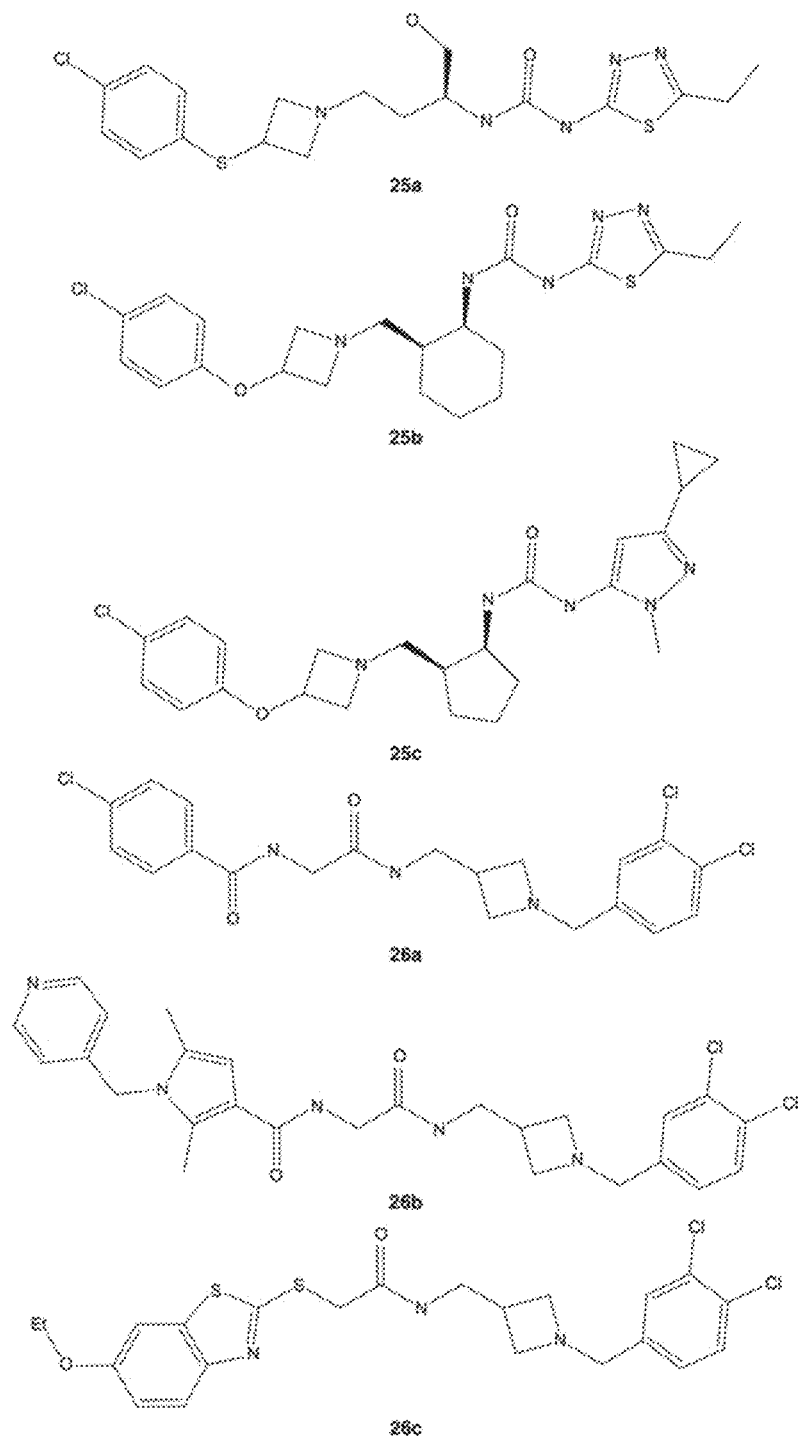
FIG. 18 shows examples of other small molecule CCR3 antagonists that can be used in non-limiting embodiments of the present disclosure.
Figure 19:
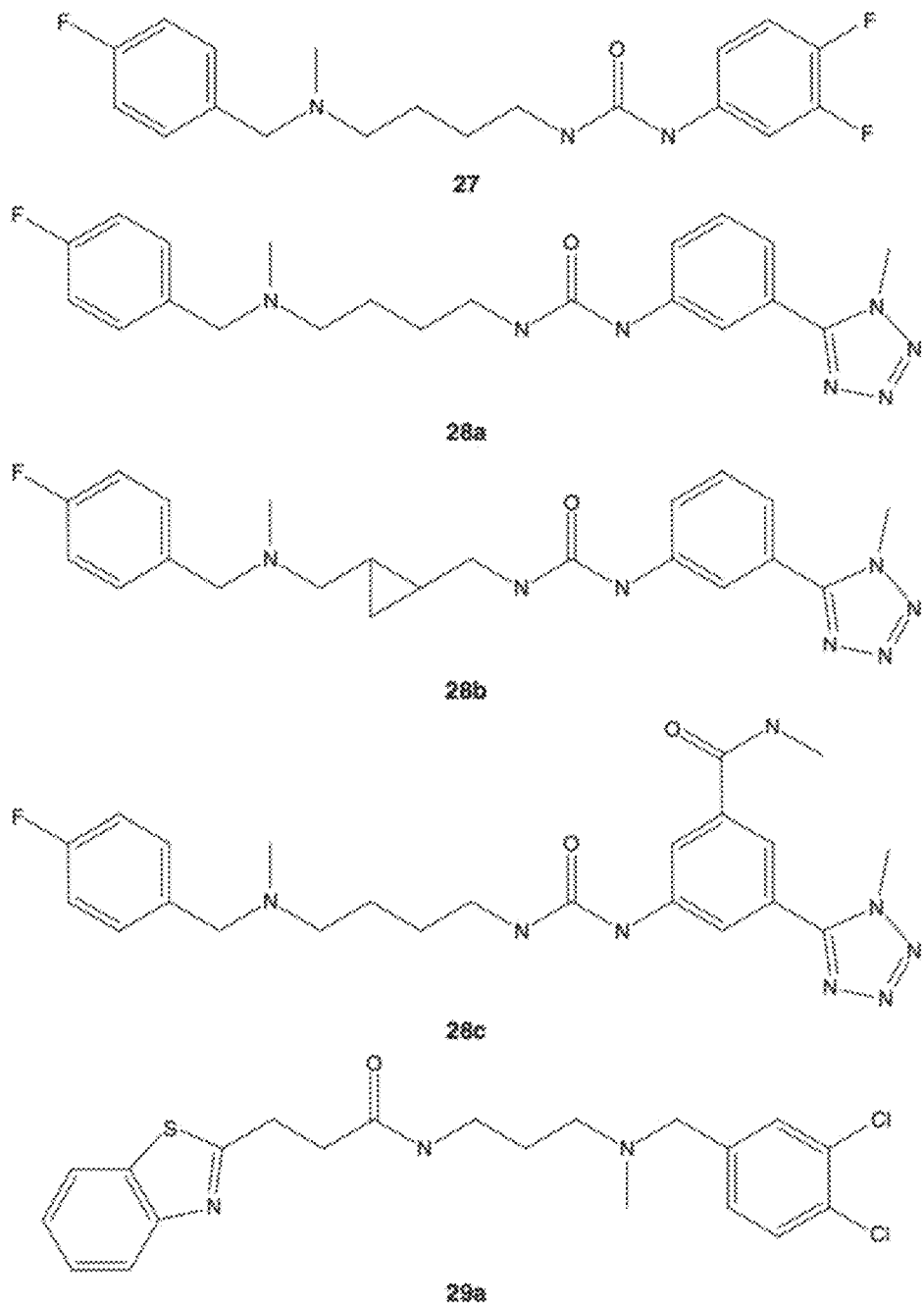
FIG. 19 shows examples of other small molecule CCR3 antagonists that can be used in non-limiting embodiments of the present disclosure.
Figure 20:
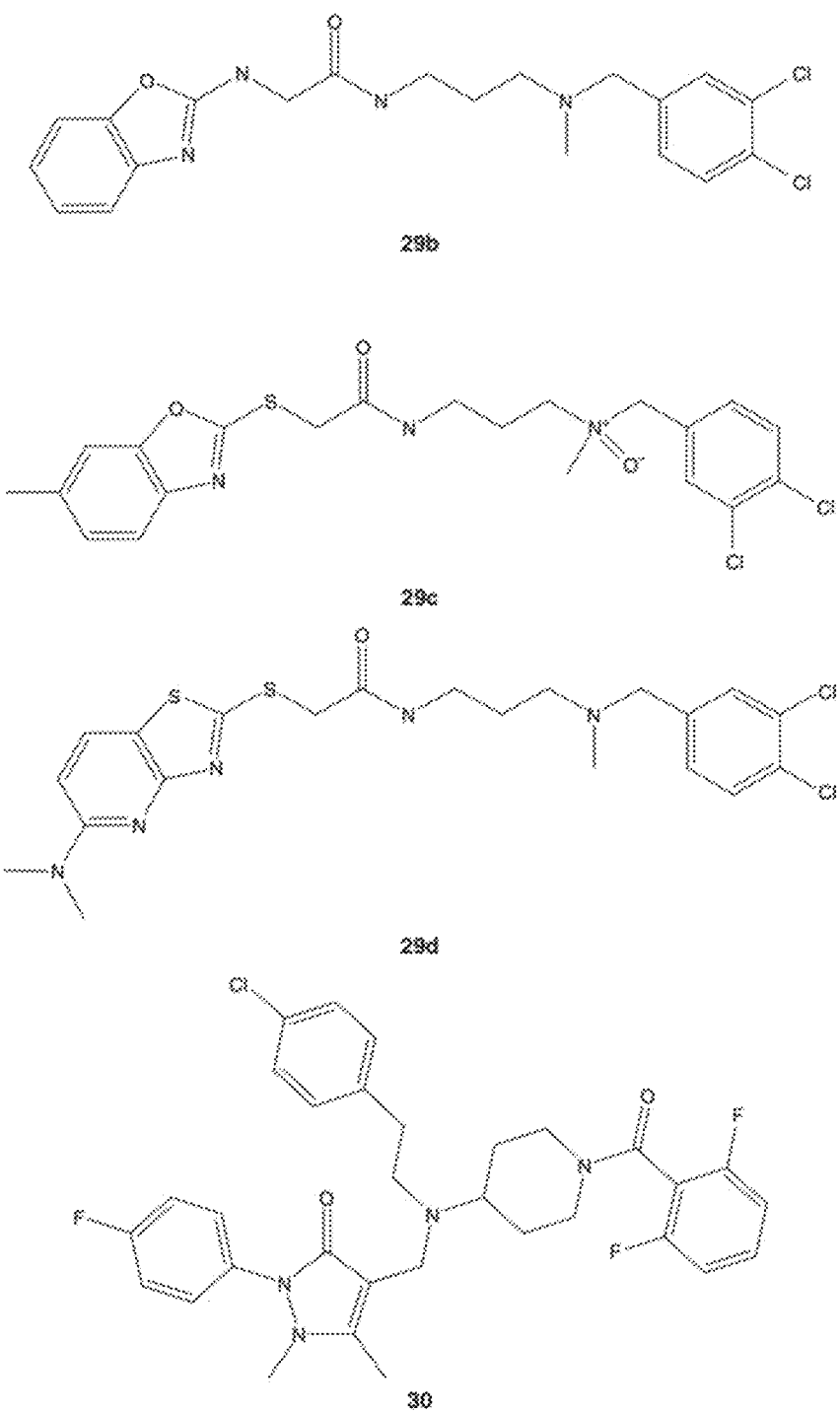
FIG. 20 shows examples of other small molecule CCR3 antagonists that can be used in non-limiting embodiments of the present disclosure.
Figure 21:
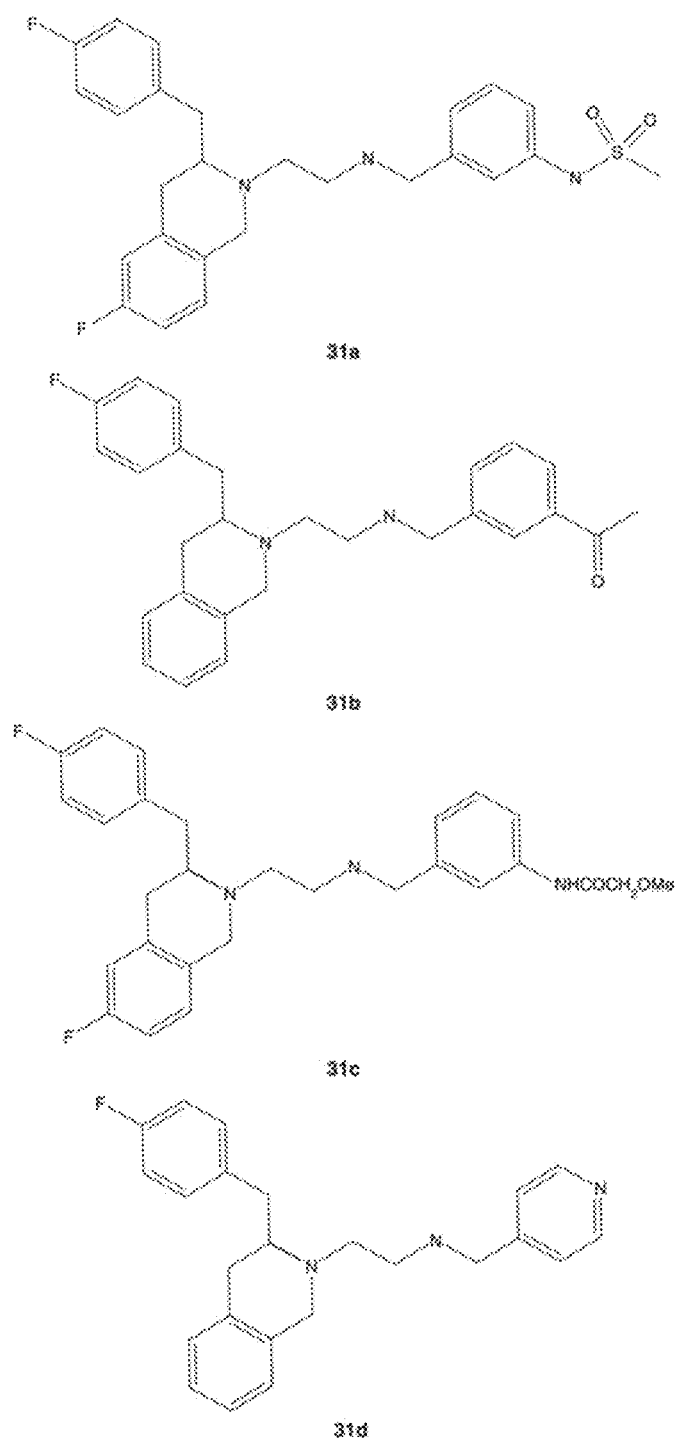
FIG. 21 shows examples of other small molecule CCR3 antagonists that can be used in non-limiting embodiments of the present disclosure.
Figure 22:
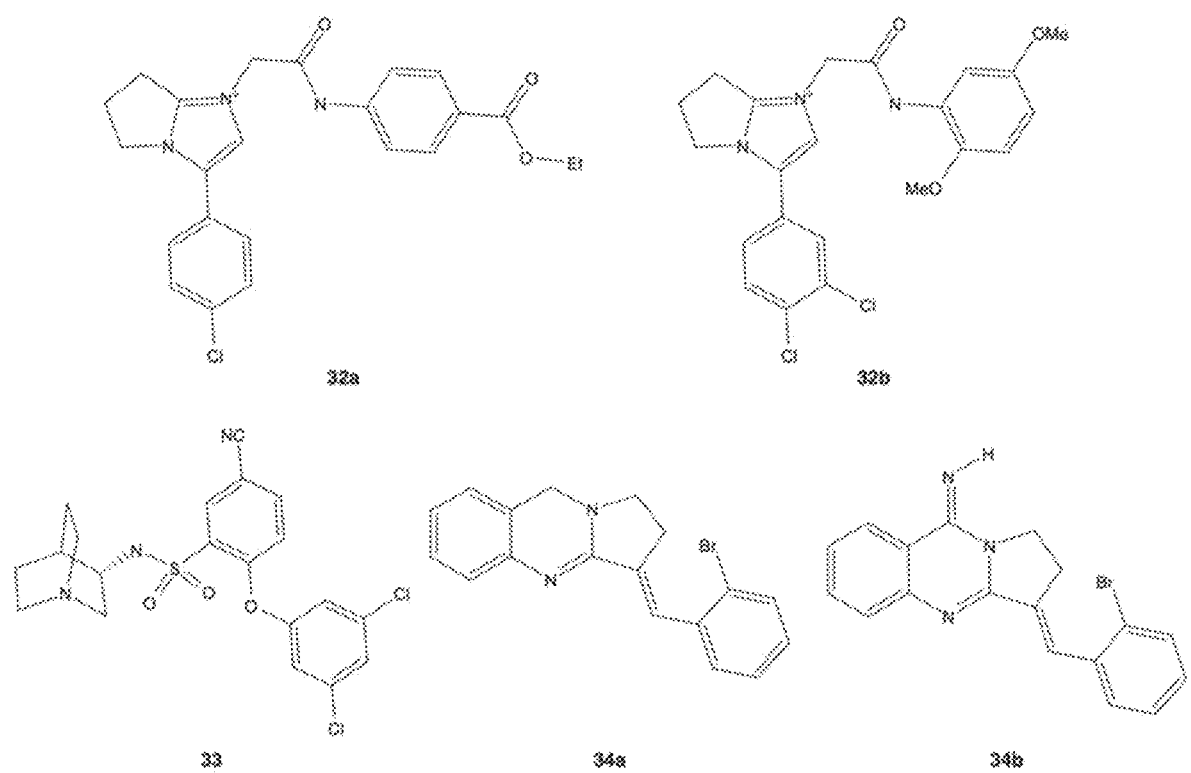
FIG. 22 shows examples of other small molecule CCR3 antagonists that can be used in non-limiting embodiments of the present disclosure.
Figure 23:
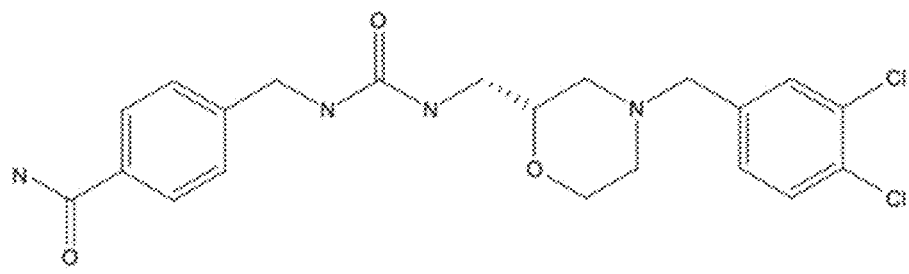
FIG. 23 shows examples of other small molecule CCR3 antagonists that can be used in non-limiting embodiments of the present disclosure.
Figure 23:
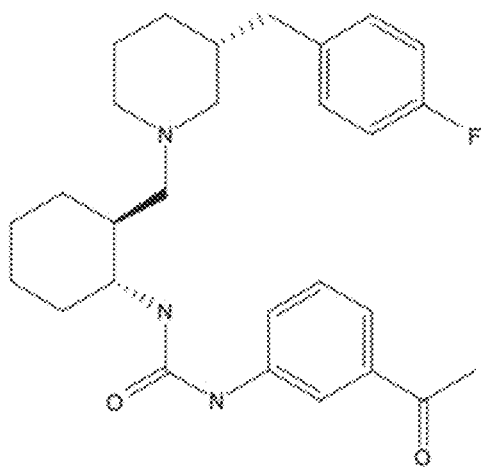
Figure 23:
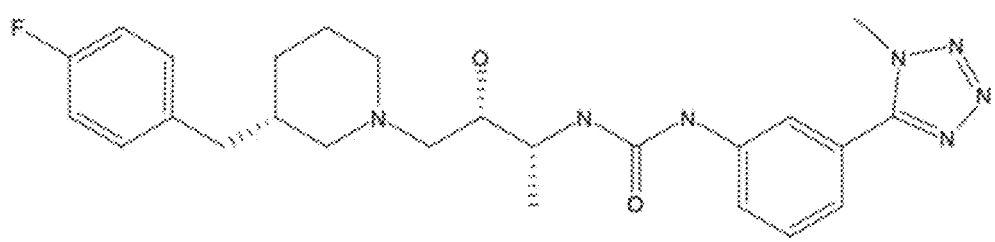

The effects of CCR3 inhibition were studied in an in vivo model of wound healing. A mouse model of delayed healing was utilized where stable hyperglycemia was induced in C57BL/6 mice via streptozotocin treatment. Mice were confirmed hyperglycemic (>300 mg/dl glucose) for eight weeks, and full thickness (4 mm) punch biopsy silicon splinted wounds were performed as described in Galiano, R. D., et al. (*Quantitative and reproducible murine model of excisional wound healing*. Wound Repair Regen, 2004. 12 (4): p. 485-92). When applied >7 days post wounding, 10 μg/wound of anti-mouse CCR3 neutralizing antibody significantly enhanced wound closure so that the wound was closed by day 11, whereas the control wound did not close until day 15, four days after closure of the wound treated by the CCR3 inhibitor (FIG. 5).

Discussion

It is well known that impaired epithelialization is a characteristic of non-healing wounds during chronic inflammation. CCR3 agonism with CCL28 was shown to promote oral wound healing (Buskermolen, J. K., S. Roffel, and S. Gibbs, *Stimulation of oral fibroblast chemokine receptors identifies CCR3 and CCR4 as potential wound healing targets*. J Cell Physiol, 2017. 232 (11): p. 2996-3005). Conversely, the results presented herein show that blockade of CCR3 augments keratinocyte wound closure in vitro (FIGS. 2A-2B) and in vivo (FIG. 5). However, gingiva oral tissue is primarily composed of fibroblasts, rather than keratinocytes. Furthermore, skin and mucosa are known to exhibit differences in proliferative and migratory capacities during wound healing (Turabelidze, A., et al., *Intrinsic differences between oral and skin keratinocytes. PLoS One*, 2014. 9 (9): p. e101480).

Following cutaneous injury, the process of epithelialization involves migration of keratinocytes from the wound edge to close the injury. Keratinocytes behind the migrating edge undergo proliferation to ensure that there is a sufficient supply for re-epithelialization. Once the epithelial layer is reformed, keratinocytes switch to a more differentiated state to restore epidermal function. Multiple regulators are necessary to modulate keratinocytes during epithelialization, but keratinocyte actions are distinguished by an infrastructure comprised of keratin (K) intermediate filaments. Migrating and proliferating keratinocytes express K16 and K17, whereas differentiated keratinocytes will express K1 and K10. In chronic wounds, keratinocytes will undergo proliferation but fail to migrate or differentiate, resulting in epidermal hyperplasia and reduced expression of K1 and K10. In the result described herein, following wounding, blockade of keratinocyte CCR3 expression was found to increase expression of K1 (FIGS. 3A and 3E), K10 (FIG. 3B), and K17 (FIGS. 3D and 3F). However, K16 (FIG. 3C) was not found to be up-regulated in wounded keratinocytes exposed to anti-CCR3, and was higher in control eight hours post-wounding. Interestingly, overexpression of K16 has been associated with delayed wound closure via impairing keratinocyte migration (Wawersik, M. J., et al., *Increased levels of keratin 16 alter epithelialization potential of mouse skin keratinocytes in vivo and ex vivo*. Mol Biol Cell, 2001. 12 (11): p. 3439-50). These results substantiate that blockade of keratinocyte CCR3 expression promotes wound closure.

Furthermore, up-regulation of K1 and K10 following inhibition of CCR3 indicate that the CCR3 receptor can be targeted for treatment of cutaneous disorders distinguished by epidermal hyperplasia, as is well known to occur in chronic eczema.

Autocrine regulation of re-epithelialization has been shown to promote wound closure, as keratinocytes utilize various chemokines in an autocrine loop to initiate migration and proliferation, but not necessarily differentiation. CCR3 has multiple ligands, but the chemokines CCL24 (eotaxin-2) and CCL26 (eotaxin-3) bind exclusively to CCR3. Herein, it was found that following in vitro wounding, keratinocytes exhibited increased mRNA expression of CCL26 (FIG. 4B), but not CCL24 (FIG. 4A). However, consistent with previous findings, CCL24 and CCL26 protein expression was not secreted at detectable levels (data not shown). Furthermore, neither treatment with CCL24 nor CCL26 was found to influence migration (FIGS. 4E-4F), which is similar to previous findings evaluating CCL24 and keratinocyte migration. Indeed, CCL24 and CCL26 were found to decrease keratinocyte proliferation (FIGS. 4C-4D). These results are inconsistent with those published by Kroeze, K. et al., illustrating that CCL24 promoted keratinocyte proliferation (Kroeze, K. L., et al., *Autocrine regulation of re-epithelialization after wounding by chemokine receptors CCR1, CCR10, CXCR1, CXCR2, and CXCR3*. J Invest Dermatol, 2012. 132 (1): p. 216-25). However, these opposing results may be due to the type of collagen the keratinocytes were cultured on, as collagen can influence many cellular functions, including migration and proliferation. In the present example, keratinocytes were plated on collagen I, as it is the most common and abundant form of collagen in healed wounds. in contrast, Kroeze, K. et al (op. cit.) utilized type IV collagen, which is primarily found within the basement membrane. As basement membrane is undisturbed in skin conditions such as chronic eczema, this indicates that blockade of CCR3 can be useful as indicated above.

Diabetic ulcers are known to display defects in nearly all phases of the wound healing process. Normal wound healing is typically broken into four overlapping phases: coagulation, inflammation, proliferation, and remodeling. Interruption of any of these phases could potentially delay healing. Herein, it is shown that blockade of CCR3 accelerates wound healing in STZ hyperglycemic mice (FIG. 5). The fact that the murine splinted wound model mediates healing primarily through reepithelialization similar to human wounds, indicates a role for CCR3 ligands to inhibit this response in hyperglycemic wounds, either through modulation of receptor function or possibly overexpression of its ligands.

Herein, it has been demonstrated that blockade of keratinocyte CCR3 augments and promotes wound closure in vitro and in vivo utilizing a mouse model of slow healing hyperglycemic splinted wounds. These novel findings, when viewed with the results demonstrating up-regulation of K1, K10, and K17 expression following anti-CCR3 treatment, indicate that the CCR3 receptor can be targeted for treatment of cutaneous disorders distinguished by impaired epithelialization. Thus, in at least one non-limiting embodiment, the present disclosure is directed to a method of treating non-healing diabetic wounds by administering to the wound, directly or indirectly, an inhibitor of CCR3.

It will be understood from the foregoing description that various modifications and changes may be made in the various embodiments of the present disclosure without departing from their true spirit. The description provided herein is intended for purposes of illustration only and is not intended to be construed in a limiting sense. Thus, while embodiments of the present disclosure have been described herein so that aspects thereof may be more fully understood and appreciated, it is not intended that the present disclosure be limited to these particular embodiments. On the contrary, it is intended that all alternatives, modifications and equivalents are included within the scope of the inventive concepts as defined herein. Thus, the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulations and compositions described herein, the methods described herein or in the steps or the sequence of steps of the methods described herein without departing from the spirit and scope of the present disclosure.

What is claimed is:

1. A method of treating a skin wound in a subject, comprising:
    administering to the subject at least one inhibitor selected from the group consisting of a neutralizing anti-C-C chemokine receptor type-3 (CCR3) antibody and a neutralizing anti-CCR3 fragment thereof, thereby causing increased activity of keratinocytes adjacent the skin wound, wherein epithelialization of the skin wound is increased, and wherein the increased activity of keratinocytes is at least one of (1) increased proliferation of the keratinocytes and (2) increased migration of the keratinocytes adjacent the skin wound.

2. The method of claim 1, wherein the skin wound is a chronic wound.

3. The method of claim 1, wherein the skin wound is a diabetic wound.

4. The method of claim 1, wherein the skin wound is an acute wound.

5. A method of treating a skin wound, comprising:
    administering to a subject in need of such therapy at least one inhibitor selected from the group consisting of a neutralizing anti-C-C chemokine receptor type-3 (CCR3) antibody and a neutralizing anti-CCR3 fragment thereof, wherein the at least one inhibitor is administered to the subject in an amount effective in causing increased proliferation of keratinocytes adjacent the skin wound, thereby enhancing epithelialization of the skin wound.

6. The method of claim 5, wherein the skin wound is a chronic wound.

7. The method of claim 5, wherein the skin wound is an acute wound.

8. A method of treating a skin wound, comprising:
    administering to a subject in need of such therapy at least one inhibitor selected from the group consisting of a neutralizing anti-C-C chemokine receptor type-3 (CCR3) antibody and a neutralizing anti-CCR3 fragment thereof, wherein the at least one inhibitor is administered to the subject in an amount effective in causing increased migration of keratinocytes adjacent the skin wound, thereby enhancing epithelialization of the skin wound.

9. The method of claim 8, wherein the skin wound is a chronic wound.

10. The method of claim 8, wherein the skin wound is an acute wound.

* * * * *

UNITED STATES PATENT AND TRADEMARK OFFICE
CERTIFICATE OF CORRECTION

PATENT NO. : 12,221,463 B2
APPLICATION NO. : 17/396235
DATED : February 11, 2025
INVENTOR(S) : Randle M. Gallucci and Kaitlin N. Calhoun Page 1 of 1

It is certified that error appears in the above-identified patent and that said Letters Patent is hereby corrected as shown below:

In the Specification

Column 10, Line 66: Delete "N-{43R)" and replace with -- N-{(3R) --

Column 13, Line 34: Delete "CHi" and replace with -- CH1 --

Column 26, Line 33: Delete "in" and replace with -- In --

Signed and Sealed this
First Day of April, 2025

Coke Morgan Stewart
*Acting Director of the United States Patent and Trademark Office*

```
                            SEQUENCE LISTING

<160> NUMBER OF SEQ ID NOS: 14

<210> SEQ ID NO 1
<211> LENGTH: 20
<212> TYPE: DNA
<213> ORGANISM: artificial sequence
<220> FEATURE:
<223> OTHER INFORMATION: CCR3 5' primer

<400> SEQUENCE: 1
atgctggtga cagaggtcat                                                  20

<210> SEQ ID NO 2
<211> LENGTH: 20
<212> TYPE: DNA
<213> ORGANISM: artificial sequence
<220> FEATURE:
<223> OTHER INFORMATION: CCR3 3' primer

<400> SEQUENCE: 2
aggtgagtgt ggaaggctta                                                  20

<210> SEQ ID NO 3
<211> LENGTH: 20
<212> TYPE: DNA
<213> ORGANISM: artificial sequence
<220> FEATURE:
<223> OTHER INFORMATION: CCL24 3' primer

<400> SEQUENCE: 3
ggagtgggtc cagaggtaca                                                  20

<210> SEQ ID NO 4
<211> LENGTH: 20
<212> TYPE: DNA
<213> ORGANISM: artificial sequence
<220> FEATURE:
<223> OTHER INFORMATION: CCL24 3' primer

<400> SEQUENCE: 4
ttagcaggtg gtttggttgc                                                  20

<210> SEQ ID NO 5
<211> LENGTH: 24
<212> TYPE: DNA
<213> ORGANISM: artificial sequence
<220> FEATURE:
<223> OTHER INFORMATION: CCL26 5' primer

<400> SEQUENCE: 5
gcctgatttg cagcatcatg atgg                                             24

<210> SEQ ID NO 6
<211> LENGTH: 24
```

```
<212> TYPE: DNA
<213> ORGANISM: artificial sequence
<220> FEATURE:
<223> OTHER INFORMATION: CCL26 3' primer

<400> SEQUENCE: 6
cggatgacaa ttcagctgag tcac                                          24

<210> SEQ ID NO 7
<211> LENGTH: 22
<212> TYPE: DNA
<213> ORGANISM: artificial sequence
<220> FEATURE:
<223> OTHER INFORMATION: Keratin 1 5' primer

<400> SEQUENCE: 7
tgaccctgag atccaaaagg tg                                            22

<210> SEQ ID NO 8
<211> LENGTH: 21
<212> TYPE: DNA
<213> ORGANISM: artificial sequence
<220> FEATURE:
<223> OTHER INFORMATION: Keratin 1 3' primer

<400> SEQUENCE: 8
ccgaatccaa ccgagattga t                                             21

<210> SEQ ID NO 9
<211> LENGTH: 22
<212> TYPE: DNA
<213> ORGANISM: artificial sequence
<220> FEATURE:
<223> OTHER INFORMATION: Keratin 10 5' primer

<400> SEQUENCE: 9
atgcagaatc tgaatgaccg ct                                            22

<210> SEQ ID NO 10
<211> LENGTH: 21
<212> TYPE: DNA
<213> ORGANISM: artificial sequence
<220> FEATURE:
<223> OTHER INFORMATION: Keratin 10 3' primer

<400> SEQUENCE: 10
aagtcatcag ctgccagcct t                                             21

<210> SEQ ID NO 11
<211> LENGTH: 21
<212> TYPE: DNA
<213> ORGANISM: artificial sequence
<220> FEATURE:
<223> OTHER INFORMATION: Keratin 16 5' primer

<400> SEQUENCE: 11
acacatccgt ggtgctatcc a                                             21

<210> SEQ ID NO 12
<211> LENGTH: 21
<212> TYPE: DNA
<213> ORGANISM: artificial sequence
<220> FEATURE:
<223> OTHER INFORMATION: Keratin 16 3' primer

<400> SEQUENCE: 12
```

```
ggttggcaca ctgcttcttg a                                              21

<210> SEQ ID NO 13
<211> LENGTH: 21
<212> TYPE: DNA
<213> ORGANISM: artificial sequence
<220> FEATURE:
<223> OTHER INFORMATION: Keratin 17 5' primer

<400> SEQUENCE: 13
gctcagcatg aaagcatccc t                                              21

<210> SEQ ID NO 14
<211> LENGTH: 21
<212> TYPE: DNA
<213> ORGANISM: artificial sequence
<220> FEATURE:
<223> OTHER INFORMATION: Keratin 17 3' primer

<400> SEQUENCE: 14
ttccacaatg gtacgcacct g                                              21
```